United States Patent [19]

Morrison et al.

[11] Patent Number: 5,789,161
[45] Date of Patent: Aug. 4, 1998

[54] METHODS FOR GENOME IDENTIFICATION USING DIRECT LABEL PROBE COMPOSITION

[75] Inventors: Larry E. Morrison, Glen Ellyn; Mona S. Legator, Chicago; Michael L. Bittner, Naperville, all of Ill.

[73] Assignee: AMOCO Corporation, Chicago, Ill.

[21] Appl. No.: 472,865

[22] Filed: Jun. 7, 1995

Related U.S. Application Data

[60] Division of Ser. No. 279,285, Jul. 22, 1994, abandoned, and a continuation-in-part of Ser. No. 585,876, Sep. 20, 1990, abandoned.

[51] Int. Cl.[6] .............................. C07H 21/04; C12Q 1/68
[52] U.S. Cl. .............................. 435/6; 536/22.1; 536/23.1; 536/24.3; 536/25.3; 536/25.4; 536/25.32; 536/55.3; 935/77; 935/78
[58] Field of Search .............................. 435/6; 536/22.1, 536/23.1, 24.3, 25.3, 25.4, 25.32, 55.3; 935/77, 78

[56] References Cited

U.S. PATENT DOCUMENTS 5,447,841  9/1995  Gray et al. .............................. 435/6
5,491,224  2/1996  Bittner et al. .............................. 536/22.1
5,506,350  4/1996  Bittner et al. .............................. 536/55.3

FOREIGN PATENT DOCUMENTS 0430402  6/1991  European Pat. Off. .............................. 435/6

OTHER PUBLICATIONS

Schwarzacher et al., Annals of Botany 64:315-324, 1989.

*Primary Examiner*—W. Gary Jones
*Assistant Examiner*—Paul B. Tran
*Attorney, Agent, or Firm*—William E. Murray

[57] ABSTRACT

Direct label probe compositions which counterstain genomic DNA are provided that comprise mixed DNA segments which are covalently bound to fluorophore groups through linking groups. The mixed DNA segments are derived from the total genomic DNA of a multi-chromosomal organism, especially man, and the segment mixture is approximately representative of such total genomic DNA. These probe compositions can be used concurrently or sequentially with other probe compositions. Instead of intercalating with DNA as in prior art chemical counterstains, these probe compositions hybridize with complementary segments that are present in the genomic DNA of a specimen.

16 Claims, 6 Drawing Sheets

$a = 0.4 \mu m$

⊢⊣ ⊢—10μm

⊢⊣ ⊢—10μm

⊢⊣ ⊢—10μm

METHODS FOR GENOME IDENTIFICATION USING DIRECT LABEL PROBE COMPOSITION

RELATED APPLICATION

This application is a division of U.S. patent application Ser. No. 08/279,285, filed Jul. 22, 1994, now abandoned, and is a continuation-in-part of U.S. patent application Ser. No. 07/585,876, filed Sep. 20, 1990, now abandoned.

FIELD OF THE INVENTION

This invention relates to probe compositions for genome identification, to processes for making the same, and to compositions and methods for using the same.

BACKGROUND OF THE INVENTION

Conventional fluorescence microscopy of chromosome mixtures can involve the use of chemical-type nucleotide counterstains comprised of color-group-containing compounds which either intercalate between the bases of DNA or bind to the outside of the DNA helix. Such counterstains are desirable, for example, in in situ DNA hybridizations to enhance the visualizing of nonspecific chromosomal regions, such as regions that are not being specifically hybridized with a particular fluorophore-labeled probe. The counterstain color should preferably contrast with the color associated with the probe. With fluorescent probes, the counterstain is preferably fluorescent. Examples of chemical fluorescent counterstains currently in use include 4',6-diamidino-2-phenylindole dihydrochloride hydrate (DAPI), propidium iodide (PI), quinacrine mustard, and the like. Typically such stains display variations in color intensity from one region of a chromosome to another.

Such chemical counterstains suffer from various disadvantages. For one thing, only a few of such fluorescent counterstains are available, thereby limiting the available selection of spectral properties, including excitation and emission wavelengths, and the spectral widths of absorbing and emitting bands.

For another thing, in cytological usage, such counterstains typically produce a coloration intensity which does not correlate with, or proportionately correspond to, the capacity, or ability, of a cell nucleus, or chromosome, to undergo, or be accessible to, hybridization. For example, a low level of counterstaining could be used as a criterion for rejecting particular nuclei, thereby avoiding the undercounting of chromosomes or chromosomal regions. Such a correlation is important for purposes of "scoring" nuclei for the presence, absence, or number of specific chromosomes or chromosomal regions per nucleus. Poor accessibility of a nucleus to hybridization probes, which are typically expensive, would lead to waste and to inaccuracy caused by undercounting of the chromosomes or chromosomal regions and a consequential misdiagnosis.

For another thing, such prior art chemical counterstains, apparently owing to their method of association with DNA (as above indicated), can sometimes interfere with the capacity of probes to hybridize with target DNA, as in a second round of hybridizations, or perhaps in a subsequent banding procedure, after a first hybridization.

An indirect label probe composition, wherein a total human DNA was labeled using mercuric acetate, was taught by Hopman et al. in Histochemistry 85, 1–4 (1986) and in Experimental Cell Research 169, 357–386 (1987). However, Hopman et al. do not use or propose the use of such probes as general counterstains. Also, after in situ hybridization, the hybrids formed therewith had to be further processed to make them detectable. Thus, in one case, thiol-containing labels were detected with a labeled antibody, while in another case, thiolated fluorescein was incubated with the hybrids following in situ hybridization. Secondary processing with reagents such as thiolated fluorescein might interfere with other hybridization probes and/or other secondary reactions required to visualize the other probes. Also the secondary processing complicates and lengthens the assay. A one-step type hybridization procedure for achieving genomic DNA counterstaining without additional manipulations is not taught or suggested by Hopman et al.

The art of in situ hybridization needs a new and improved class of genomic counterstaining compositions which avoids such disadvantages.

SUMMARY OF THE INVENTION

This invention provides (a) a new and very useful class of DNA probe compositions which are useful as directly detectable genomic DNA counterstains for chromosome detection and the like in in situ hybridization and the like, particularly involving the human genome, and (b) processes for making and using such probes.

These novel, direct label, genomic DNA counterstaining probe compositions employ nucleotide segments comprised of, or derived from, the total genomic DNA of a genome, particularly a genome that is to undergo, or is undergoing, an in situ hybridization or other procedure. Such segments in such a probe composition are labeled with chemically bound fluorophores by using a preparation procedure such as is provided herewith.

A presently preferred genome for use in the practice of this invention is the human genome.

A presently preferred fluorophore label for use in any given inventive probe composition is one which is spectrally distinct from the fluorophore label employed in any other direct or indirect label probe or probe composition that is being used either concurrently, or sequentially, with such a probe composition of this invention for purposes of carrying out a particular in situ hybridization involving the genomic DNA.

In a probe composition of this invention, the DNA thereof is in the form of mixed segments that are derived from fragmented DNA sequences which individually occur at various locations throughout the total genome under consideration. Such sequences are obtained from either the genomic DNA itself or a copy thereof. Such a copy can be produced, as those skilled in the art will appreciate, by using a procedure such as cloning, enzymatic amplification, a combination thereof, or the like, as desired.

So far as is known, no one has heretofore provided a probe composition of fluorophore group-direct labeled DNA segments comprised of fragmented DNA sequences which taken together comprise the total genomic DNA of a given genome. Such DNA segments are typically in the average size range of about 150 to about 600 base pairs (bp), although larger and smaller such fragmented segments can be used, if desired. More preferably, such fragmented DNA segments are in the average size range of about 200 to about 400 bp, and most preferably have an average size of about 300 base pairs. Such segments are conveniently produced from the starting total genomic DNA sequences by a conventional sequence fragmentation procedure, and a presently preferred procedure involves sonication.

This invention further provides processes for making such probe compositions. Thus, to label starting DNA segments and thereby produce the desired direct label probe compositions, linking groups with reactive terminals are first introduced thereinto, and then fluorophore groups are covalently bonded to these terminals.

A product direct label probe composition of this invention can hybridize with all or any portion (i.e., fraction) of the genome under consideration that is present in a target composition. The hybridizing is accomplished under hybridizing conditions in an in situ hybridization or the like with a specimen containing target DNA comprised of all or a part of the genome utilized in such product probe composition. The hybrids produced are associated with the target genomic DNA that is present in the specimen and cause the individual body or bodies of such target DNA to have the visual appearance of being substantially completely stained when viewed with fluorophore exciting radiation under a fluorescence microscope or the like, or when examined with flow cytometric analysis or the like.

Hybrids produced with such a product direct labeled probe composition of this invention can be directly detected after their formation with target DNA following such a hybridization procedure. Thus, a product probe composition can be employed as a total or general genome counterstain in any in situ hybridization involving as a target the genome or a fraction thereof. The probe composition of this invention can thus be used to detect, identify, (including detect, visualize and/or quantify) nonspecific chromosome regions in a cytological or histological specimen. Such a visualization may be enhanced by using fluorophore moieties whose color is adapted for contrasting with the color of other fluorophore moieties which may be present in a specimen for other DNA identification purposes.

Another advantage of the present probe compositions is that a relatively large number of fluorophore group-containing compounds are known which can be associated as taught herein with starting genomic DNA sequence fragments. Thus, a greater selection of spectral properties can be achieved within a given probe composition of the present invention than is possible with the prior art chemical counterstains. The choice of counterstain fluorophore group color employed in a probe composition of this invention can be tailored to enhance contemplated probe composition usage with one or more other chromosomal target-specific nucleic acid probes.

Another advantage of the probe compositions of this invention is that the component probes do not intercalate, so that second hybridizations, banding procedures, or the like can be carried out subsequently to, or even concurrently with, the usage thereof on or in a given DNA-containing cytological preparation.

Another advantage of the probe compositions of this invention is that they can function as indicators of the accessibility of cytological nucleic acids, especially genomic DNA, to probe nucleic acids. If a cell's DNA is not accessible to such a counterstain, then none of its DNA will be visible and so such will not be mistaken for having specific hybridizable target DNA.

Another advantage of the probe compositions of this invention is that they can be admixed with other direct labeled probe compositions, especially fluorophore labeled probes, and the resulting mixed probes can be employed in an in situ hybridization to accomplish simultaneously both genomic DNA counterstaining as well as coloration of specific genomic DNA regions or fractions without any undesirable interference or interaction resulting from such admixing. Thereby, the time and labor of performing a series of hybridization steps, including separate incubation steps, which would otherwise be necessary, is completely saved.

An important feature associated with the probe compositions of this invention is that they contain direct label probes. Thus, after hybridization thereof with genomic DNA in a specimen, and subsequent washing, counterstaining is complete. No further subsequent reactive processing with other reagents is needed to develop detectability, such as is necessary with indirect label probes. Also, indirect label probes usually have compatibility limitations; for example, they cannot be used with other probes which might contain components which will interfere with a necessary post hybridization reaction needed to develop detectable moieties. Further, the number of known reactant pairs needed for use with indirect label probes is limited so that the mixed compositions of different probes which can be prepared for subsequent in situ hybridization procedures is limited.

Another important feature of the present invention is that usage of probe compositions of this invention results in counterstained DNA which can be further processed under in situ hybridization conditions or the like without substantial removal of the hybridized counterstain from the counterstained DNA. In contrast, with prior art chemical counterstains, subsequent exposure of a stained specimen to processing liquids can result in removal, at least partially, of the stain. A principal reason for this stain stability difference is believed to be associated with the characteristically higher binding constants associated with hybrids below their melting temperature (Tm) compared with the binding constants associated with intercalated agents.

The total genomic DNA counterstaining, direct label probe compositions of this invention are also readily distinguishable from direct label regionally specific probes, such as individual chromosome DNA paint probe compositions, which cannot be used to detect any genomic DNA other than the particular genome fraction to which such paint probe composition is targeted by careful design choice because of the complementary limitations of the DNA sequences contained therein.

The ability of the fluorophore labeled probe compositions of this invention to produce clear, sharp, directly detectable, genomic chromosomal hybrids during a chromosome assay by in situ hybridization results not only in new and very useful in situ hybridization processes which employ such probes, but also in new and very useful products, such as genomic target DNA bodies which have been substantially completely counterstained with a probe composition of this invention, or hybrids which have been produced by in situ hybridization with a probe composition of this invention with a target DNA.

Other and further features, objects, aims, purposes, advantages, applications, embodiments and the like will be apparent to those skilled in the art from the teachings of the present specification taken with the accompanying drawings.

5

Figure 1:
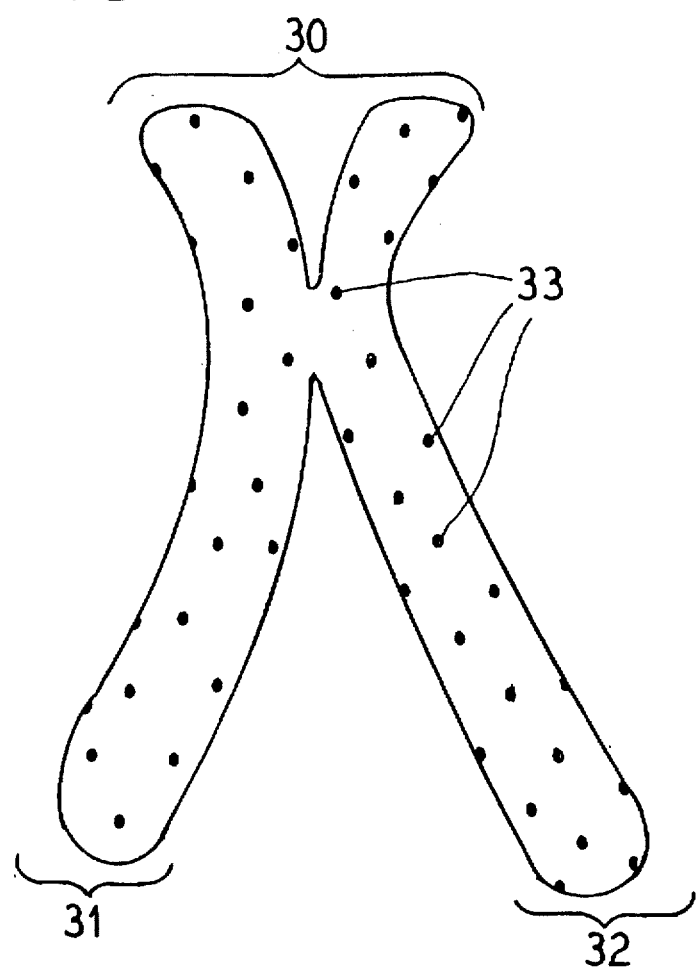
FIG. 1 is a diagrammatic, microscopic view of a single metaphase chromosome that has been counterstained by a probe composition of this invention.
Figure 4:
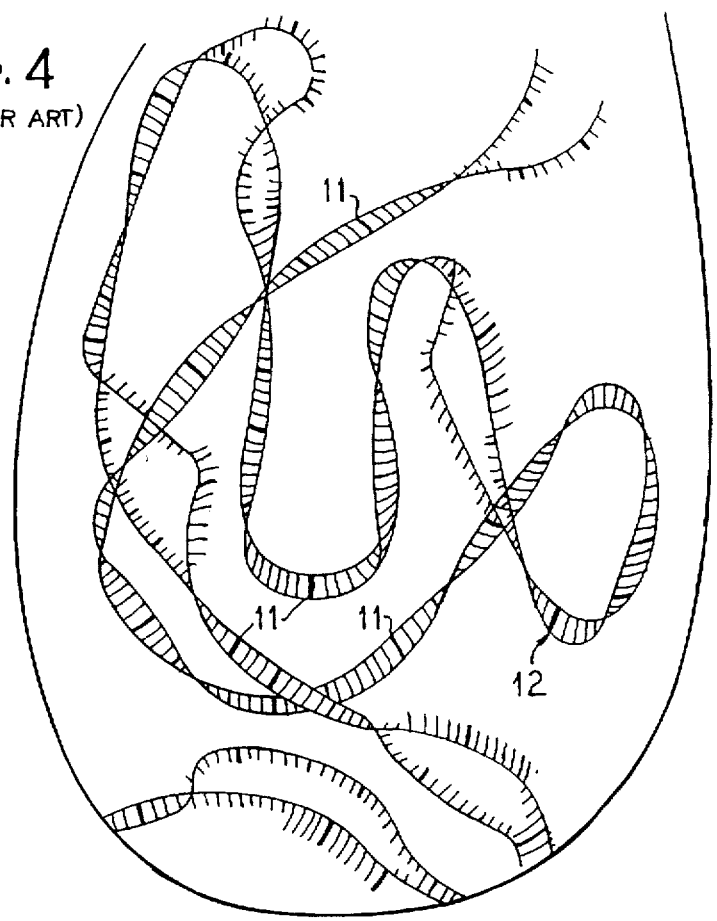
Figure 6:
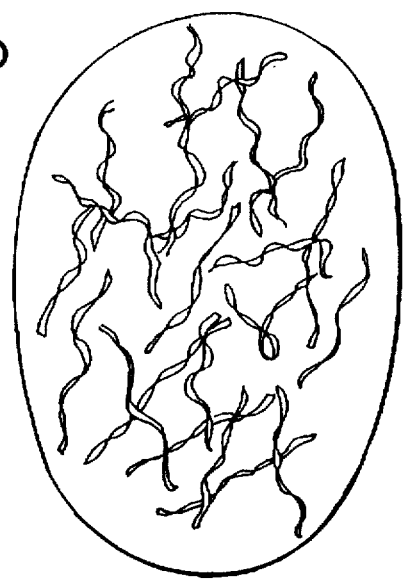
Figure 5:
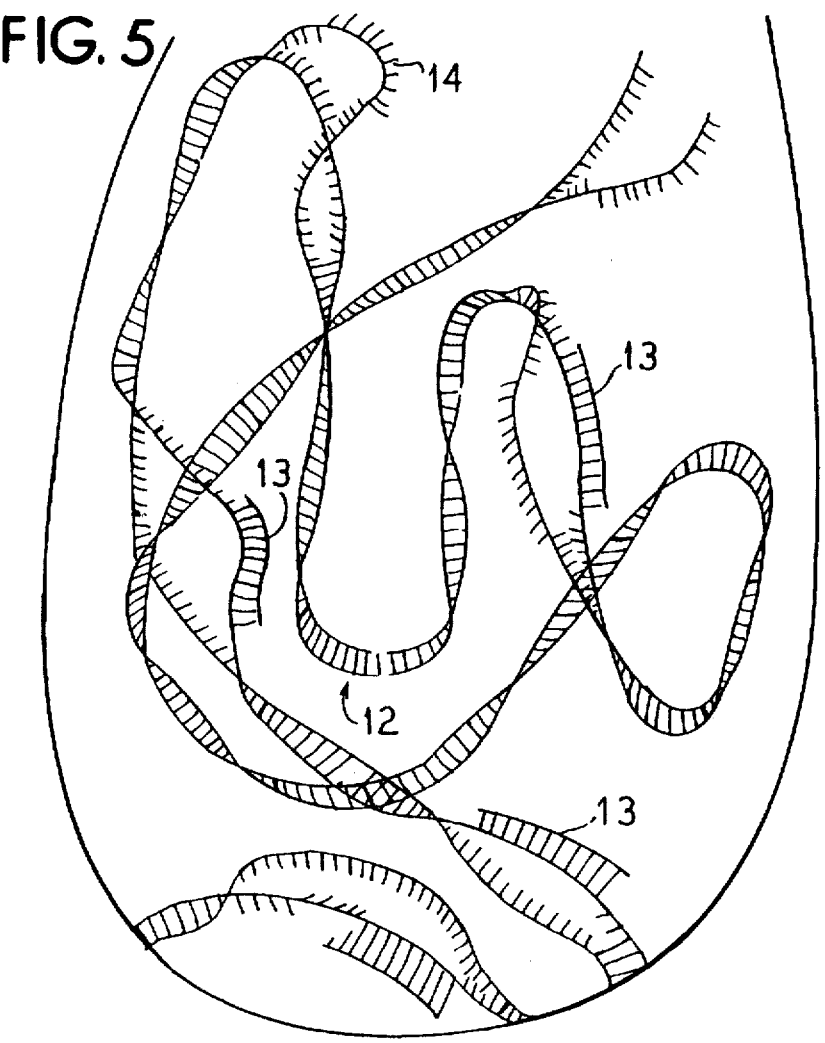

FIG. 4 is a fragmentary, greatly enlarged diagrammatic view of one region identified as II of such chromosome of FIG. 1 after such chromosome has been counterstained by a prior art intercalating genomic chemical-type DNA counterstain;

FIG. 5 is a view similar to FIG. 4 but showing such region II after such chromosome has been counterstained by a genomic DNA probe composition of the present invention;

FIG. 6 is a microscopic diagrammatic view of a slide mounted specimen of a single human cell nucleus which has been counterstained by a DNA counterstain; and FIG. 7 through 15 are photomicrographs of specimens of human metaphase and interphase DNA which have been counterstained with probe compositions of this invention.

DETAILED DESCRIPTION (A) Definitions

The term "counterstain" as used herein has general and conventional reference to a supplementary or background color produced by a staining process or the like which color takes effect on all, or a selected group of, components (or constituent bodies) of a cytological or histological preparation. Typically, such components are to undergo a microscopic examination, or the like, and typically another or other principle or primary color(s) produced by another or other stains which are selective may be involved in the examination. The main purpose or function of such a counterstain color is usually to improve or enhance such an examination.

The term "sequence" refers to a chain or interconnected series of DNA nucleotides.

The term "fragment", "segment" or "DNA segment" indicates generally only a portion of a larger DNA polynucleotide or sequence such as occurs in one chromosome or one region of a chromosome. A polynucleotide, for example, can be broken up, or fragmented into, a plurality of segments or fragments. As is known, a chromosome characteristically contains regions which have DNA sequences that contain DNA repeated segments. The term "repeated" has reference to the fact that a particular DNA segment occurs a plurality (i.e., at least two) times as the same DNA sequence, or plurality of DNA sequences. Individual DNA segment size and/or DNA repeated segment size can vary greatly. For example, in the case of the human genome, each DNA repeated segment is now believed to be typically in the approximate size range of about 5 to about 3,000 bp. Illustratively, a single chromosome alphoid DNA sequence may incorporate at least about five different DNA repeated segments.

The term "genome" designates or denotes the complete, single-copy set of genetic instructions for an organism as coded into DNA of the organism. In the practice of the present invention, the particular genome under consideration is typically multi-chromosomal so that such DNA is cellularly distributed among a plurality of individual chromosomes (which number, for example, in humans 22 pairs plus a gender associated XX pair or an XY pair).

In the practice of this invention, the genome involved in any given instance is preferably from a primate, and the DNA sequences of a preselected chromosome from such a genome contain DNA repeated segments that are inclusive of either alphoid DNA or are associated with the centromere of the preselected chromosome. As used herein, the term "alphoid" or "alpha satellite" in reference to DNA has reference to the complex family of tandemly repeated DNA segments found in primate genomes. Long tandem arrays of alpha satellite DNA based on a monomer repeat length of about 171 base pairs are located principally at the centromeres of primate chromosomes.

The term "chromosome" refers to a heredity-bearing gene carrier of a living cell which is derived from chromatin and which comprises DNA and protein components (especially histones). The conventional internationally recognized individual human genome chromosome numbering identification system is employed herein. The size of an individual chromosome can vary from one type to another with a given multi-chromosomal genome and from one genome to another. In the case of the (preferred) human genome, the entire DNA mass of a given chromosome is usually greater than about 100,000,000 bp. For example, the size of the entire human genome is about $3 \times 10^9$ bp. The largest chromosome, chromosome no. 1, contains about $2.4 \times 10^8$ bp while the smallest chromosome, chromosome no. 22, contains about $5.3 \times 10^7$ bp (Yunis, J. J. *Science* 191:1268–1270 (1976), and Kavenoff, R., et al. *Cold Spring Harbor Symposia on Quantitative Biology* 38:1–8 (1973)).

The term "region" indicates a portion of one chromosome which contains DNA repeated segments that are preferably alphoid or associated with the centromere. The actual physical size or extent of such an individual region can vary greatly. An exact quantification of such a region cannot now be made for all possible regions. Usually, a region is at least large enough to include at least one DNA sequence that (a) incorporates a plurality of copies of at least one DNA repeated segment and that (b) is identifiable and preferably enumeratable optically by fluoroscopic microscopic examination after formation of fluorophore labeled hybrids in such region following an in situ hybridization procedure with a direct label probe or probe composition. Presently available information suggests that a region may contain more than a single such DNA sequence with each such DNA sequence containing one or more DNA repeated segments.

The term "region" is typically and characteristically a chromosome fragment which comprises less DNA mass or size than the entire DNA mass or size of a given chromosome. As is known, not all the DNA of a given chromosome or chromosome region is arranged as DNA sequences comprised of or containing DNA repeated segments. A region, for example, can have a size which encompasses about $2 \times 10^6$ to about $40 \times 10^6$ DNA bp. which size region encompasses, for example, centromeres of the human chromosomes. Such a size is thus a substantial fraction of the size of a single human chromosome. Such a region size is presently preferred as a region size in the practice of this invention although larger and smaller region sizes can be used. A centromeric region of even a small human chromosome is a microscopically visible large portion of the chromosome, and a region comprising DNA repeated segments (not alphoid or centromeric) on the Y chromosome occupies the bulk of the chromosome and is microscopically visible. In general, the term "region" is not definitive of a particular one (or more) genes because a "region" does not take into specific account the particular coding segments (exons) of an individual gene. Rather, a "region" as used herein in reference to a chromosome is unique to a given chromosome by reason of the particular combination of DNA segments therein for present probe composition formation and use purposes.

The term "centromere" refers to a heterochromatic region of the eucaryotic chromosome which is the chromosomal site of attachment of the kinetochore. The centromere divides just before replicated chromosomes separate, and so such holds together the paired chromatids.

The term "gene" designates or denotes a DNA sequence along a chromosome that codes for a functional product (either RNA or its translation product, a polypeptide). A gene contains a coding region and includes regions preceding and following the coding region (termed respectively "leader" and "trailer"). The coding region is comprised of a plurality of coding segments ("exons") and intervening sequences ("introns") between individual coding segments.

The term "probe" or "probe composition" refers to a polynucleotide, or a mixture of polynucleotides, such as DNA sequence(s) or DNA segment(s) which has (or have) been chemically combined (i.e., associated) with individual label-containing moieties. Each such polynucleotide of a probe is typically single stranded at the time of hybridization to a target.

The term "label" or "label containing moiety" refers in a general sense to a moiety, such as a radioactive isotope or group containing same, and nonisotopic labels, such as enzymes, biotin, avidin, streptavidin, digoxygenin, luminescent agents, dyes, haptens, and the like. Luminescent agents, depending upon the source of exciting energy, can be classified as radioluminescent, chemiluminescent, bioluminescent, and photoluminescent (including fluorescent and phosphorescent).

Probe compositions of this invention contain DNA segments that are chemically bound to label-containing moieties. Each label-containing moiety contains at least one fluorophore (fluorescent) group, and each label-containing moiety is derived from a monofunctional reactive substituent-containing, and also fluorophore substituent containing, starting fluorescent compound, as hereinbelow more particularly described.

The term "direct label probe" (or "direct label probe composition") designates or denotes a nucleic acid probe whose label after hybrid formation with a target is detectable without further reactive processing of hybrid. Probe compositions of this invention are of the direct label type.

The term "indirect label probe" (or "indirect label probe composition") designates or denotes a nucleic acid probe whose label after hybrid formation with a target must be further reacted in subsequent processing with one or more reagents to associate therewith one or more moieties that finally result in a detectable entity.

The term "target", "DNA target" or "DNA target region" refers to one nucleotide sequence which occurs at a specific chromosomal location. Each such sequence or portion is typically and preferably at least partially single stranded (i.e. denatured) at the time of hybridization. When the target nucleotide sequences are located only in a single region or fraction of a given chromosome, the term "target region" is sometimes applied. Targets for hybridization can be derived from specimens which include but are not limited to chromosomes or regions of chromosomes in normal, diseased or malignant human or other animal or plant cells, either in interphase or at any state of meiosis or mitosis, and either extracted or derived from living or postmortem tissues, organs or fluids; germinal cells including sperm and egg cells, seeds, pollen or zygotes, embryos, chorionic or amniotic cells, or cells from any other germinating body; cells grown in vitro, from either long-term or short-term culture, and either normal, immortalized or transformed; inter- or intraspecific hybrids of different types of cells or differentiation states of these cells; individual chromosomes or portions of chromosomes, or translocated, deleted or other damaged chromosomes, isolated by any of a number of means known to those with skill in the art, including libraries of such chromosomes cloned and propagated in prokaryotic or other cloning vectors, or amplified in vitro by means well known to those with skill; or any forensic material, including but not limited to semen, blood, hair or other samples.

The term "hybrid" refers to the product of a hybridization procedure between a probe and a target. Typically, a hybrid is a molecule that includes a double stranded, helically configured portion comprised of complementarily paired single stranded molecules, such as two DNA molecules, one of which is a target DNA nucleotide sequence, and the other of which is the labeled DNA nucleotide sequence of a probe.

The term "stain", "selective stain", "selectively stained" or equivalent refers generally to a localized area color achieved by a staining procedure or the like which color takes effect on a selected group of components (or constituents) of a cytological or histological preparation. Typically, such colored components are to undergo a microscopic examination, or the like. Commonly another or other supplementary or background color (i.e., stain) may be involved, such as a so-called counterstain which takes effect on all components of a larger class within which a selectively stained group of components falls. The main purpose of a stain is to enhance or make possible identification of components during such an examination. A probe composition of this invention under hybridizing conditions produces hybrids which in effect stain a target chromosome or target chromosomal region with a fluorophore group.

The term "fluorescent" (and equivalent terms) has general reference to the property of a substance (such as a fluorophore) to produce light while it is being acted upon by radiant energy, such as ultraviolet light or x-rays.

The term "fluorescent compound" or "fluorophore group" generally refers to an organic moiety. A fluorescent compound is capable of reacting, and a fluorophore group may have already reacted, with a linking group. A fluorescent compound may include an organic chelator which binds a luminescent inorganic ion such as a rare earth like terbium, europium, ruthenium, or the like.

The term "linking compound" or "linking group" as used herein generally refers to a hydrocarbonaceous moiety. A linking compound is capable of reacting, and a linking group may have already reacted, with a nucleotide sequence (or nucleotide segment). A linking compound is also capable of reacting, and a linking group may have already reacted, with a fluorophore compound.

The term "in situ" means that the chromosomes are exposed from the cell nucleus without substantial disruption or relocation of the chromosomes with respect to each other and with the chromosomes being accessible to fluorescently labeled DNA probes.

The term "denaturation" or "denature" has reference to the at least partially complete conversion of a polynucleotide from a multi-stranded (or double-stranded) state to a single stranded state. The presence of an agent or agents which in effect lowers the temperature required for denaturation and for subsequent hybridizing conditions between probe (or probe composition) and target is generally desirable, and a presently most preferred such agent is formamide. Using, for example, about 50:50 volume ratio mixture of water and formamide, an illustrative temperature for thermal denaturation is in the range of about 70 to about 80 degrees C. applied for times that are illustratively in the range of about 1 to about 10 minutes.

The term "in situ hybridization" has reference to hybridization of a probe to a target that exists within a cytological or histological preparation or specimen. As a result of an in situ hybridization procedure, hybrids are produced between a probe and a target. This term "in situ hybridization" may be inclusive of denaturation and may also be inclusive of a hybrid or probe detection procedure which is practiced after in situ hybridization of a probe to a target. A specimen can be adhered as a layer upon a slide surface, and a specimen can, for example, comprise or contain individual chromosomes or chromosome regions which have been treated to maintain their morphology under, for example, denaturing conditions, or conditions such as typically exist during a flow cytometric analysis in a probe detection procedure. The term "in situ hybridization" may include use of a counterstain. In the case of the inventive fluorophore labeled probes or probe compositions, the detection method can involve fluorescence microscopy, flow cytometry, or the like.

The term "hybridizing conditions" has general reference to the combinations of conditions that are employable in a given hybridization procedure to produce hybrids, such conditions typically involving controlled temperature, liquid phase, and contacting between a probe (or probe composition) and a target. Conveniently and preferably, at least one denaturation step precedes a step wherein a probe or probe composition is contacted with a target. Alternatively, a probe can be contacted with a specimen comprising a DNA target region and both subjected to denaturing conditions together as described by Bhatt et al. (1988) in *Nucleic Acids Research* 16:3951–3961. Using, for example, about a 50:50 volume ratio mixture of water and formamide, an illustrative temperature for contacting and hybridization between probe (or probe composition) and target is in the range of about 35° to about 55° C. applied for a time that is illustratively in the range of about 1 to about 18 hours. Other hybridizing conditions can be employed. The ratio of numbers of probes to number of target sequences or segments can vary widely, but generally, the higher this ratio, the higher the probability of hybrid formation under hybridizing conditions within limits.

The term "complete", "completely", "substantially complete" or "substantially completely" refers to the capacity of a direct label probe composition of this invention to hybridize with a target so that the target body or bodies is/are highlighted and identifiable (by a fluorescence microscope, a flow cytometer, or the like) after hybridization therewith to an extent at least sufficient to show (i.e., stain or identify) the target's full extent (morphology). Thus, variations in fluorescence coloration intensity may sometimes be present (i.e., observed) in an individual hybridized chromosomal target body, but the target body as a whole is substantially highlighted.

The term "lower" refers to an individual compound, group or radical means that such compound, group or radical contains less than 6 carbon atoms.

The term "paint probe" or "painting probe", (or "paint probe composition" or "painting probe composition") refers to a probe or probe composition, such as a probe composition of this invention, which is adapted to hybridize under hybridizing conditions with a target which comprises one predetermined (i.e., preselected) chromosome of a multichromosomal genome. If only a fractional part of such one chromosome happens to be present in a specimen undergoing such a hybridization with such a probe composition, then such fractional part so hybridizes and is identified. Typically, one paint probe of this invention can be admixed with a second so as to make possible the simultaneous staining and detection of two predetermined chromosomes.

The term "clone", "cloning" or equivalent refers to the process wherein a particular nucleotide segment or sequence is inserted into an appropriate vector, the vector is then transported into a host cell, and the vector within the host cell is then caused to reproduce itself in a culturing process, thereby producing numerous copies of each vector and the respective nucleotide sequence that it carries. Cloning results in the formation of a colony or clone (i.e., group) of identical host cells wherein each contains one or more copies of a vector incorporating a particular nucleotide segment or sequence. The nucleotide segment or sequence is now said to be "cloned", and the product nucleotide segments or sequences can be called "clones".

The term "blocking DNA" or "blocking DNA composition" refers to a DNA which has the capacity, under hybridizing conditions, to hybridize with nonspecific binding DNA present in a probe. A blocking DNA composition is comprised of a mixture of DNA segments that are derived from, include, and are preferably representative of, the total genomic DNA of a multi-chromosomal genome that is under consideration and which incorporates a target. Such segments can, for example, be prepared by fragmenting (as taught herein) DNA sequences comprising or representative of such total genomic DNA, and such DNA segments so prepared are complementary to DNA segmental portions occurring throughout the chromosomes (including the regions) of this genome, such segments can also be prepared, for example, from a total genomic DNA, by other procedures, such as by a procedure involving the procedural steps of denaturing partially reannealing or re-hybridizing, and treating with enzymes, thereby to reduce the quantity of non-repeated segments therein. Blocking DNA is at the time of use with a probe composition preferably in the form of segments having average sizes in the range of about 150 to about 600 base pairs.

The term "library" is used herein in its conventional sense to refer to a set of cloned DNA fragments which together represent an entire genome or a specified fragment thereof, such as a single chromosome. Various libraries are known to the prior art and are available from various repositories, and techniques for genome and genome fragment preparation, and for cloning libraries therefrom, are well known. A present procedural preferences is to fragment a selected one chromosome that was separated by flow sorting or the like. Fragmentation prior to cloning is preferably achieved by digestion with restriction endonucleases or the like. This procedure produces fragment ends which are particularly amenable to insertion into vectors. However, those skilled in the art will appreciate that any conventional or convenient technique for fragmentation can be used. The fragments are then conventionally cloned to produce a chromosome library.

The term "blocked probe composition" has reference to a probe composition of this invention which is in admixture with a blocking DNA composition.

The term "diluent DNA" or equivalent refers to DNA which is the same as, or is similar to the DNA that is incorporated into a particular probe composition of this invention. Diluent DNA, when admixed with transaminated polynucleotides that constitute an intermediate in the making of a probe composition of the invention, or when admixed with a product probe composition of this invention, functions to dilute the total number of labeled DNA segments that are present in a given volume or weight of a probe composition of this invention.

As those skilled in the art will appreciate, a diluent DNA can also sometimes function as a blocking DNA, and vice versa.

The term "carrier DNA" refers to DNA which functions to reduce the amount of probe DNA which is inherently lost due to such effects as absorption of probe DNA to adjacent surface portions, such as the surface portions of a container vessel wherein a probe is being stored, the surface portions of a glass slide whereon a specimen undergoing in situ hybridization is deposited, or the surface portions of cellular debris present in a specimen undergoing in situ hybridization, or the like. Carrier DNA is comprised of DNA derived from an unrelated genomic species, such as salmon sperm in admixture with DNA segments derived from the human genome. A carrier DNA may be optionally added to a hybridization solution that incorporates a probe of this invention.

The term "nonspecific binding DNA" refers to DNA which is complementary to DNA segments of a probe and which DNA occurs in at least one other position in a genome, which other position is outside of a selected chromosomal target region within that genome. An example of nonspecific binding DNA comprises a class of DNA repeated segments whose members commonly occur in more than one chromosome or chromosome region. Such common repetitive segments tend to hybridize to a greater extent than other DNA segments that are present in probe composition.

(B) Starting Materials (1) The Starting Total Genomic DNA

The starting total genomic DNA used in the practice of this invention is typically in the form of a plurality of DNA sequences which taken together contain a multiplicity of DNA segments that individually occur at various locations in and throughout the individual chromosomes of a given multi-chromosomal genome. Thus, such DNA segments individually may or may not be repeated segments. Preferably the starting component segments comprise a total genomic DNA. Although in their naturally occurring state, starting DNA sequences typically have a size much greater than about one million base pairs each, at the time of availability for use as a starting material in the practice of this invention, the total genomic DNA may already be somewhat fragmented, depending upon such factors as the methods used in separation, isolation and the like.

For purposes of preparing a given probe composition of this invention, the starting total genomic DNA of a genome can be obtained by various techniques. Thus, it can be derived or obtained from cellular DNA that is separated (including purification) from component intracellular material of an organism. Separation procedures are well known and any convenient separation procedure can be used; see, for example, J. Sambrook, E. F. Fritsch, and T. Maniatis (1989), "Molecular Cloning: A Laboratory Manual, second edition, Chapter 9, Cold Spring Harbor Laboratory Press, Cold Spring Harbor, N.Y., and references cited therein. Although any convenient source of tissue or cells can be employed, it is presently preferred to select tissue which is characteristically relatively high in total genomic DNA content and from which total genomic DNA can be efficiently separated for a given genome.

When in preparing a direct label probe composition of the invention, it is presently preferred to employ a starting total genomic DNA that is representative of a selected organism's genomic DNA. The present invention can be practiced by using a starting total genomic DNA that is derived from the genome of that organism, but wherein the component multiplicity of DNA segments do not have the same distribution, or occurrence frequency, that is characteristic of that naturally (or normally) occurring in the genome of that organism. By using a starting total genomic DNA wherein the occurrence or distribution of DNA segments is skewed, the capacity of a product probe composition to counterstain genomic DNA completely and thereby detect total genomic DNA is not destroyed, but rather is altered. The result is that the resulting hybridized target genomic DNA bodies that are present in a specimen tend to be unevenly, but still substantially completely, counterstained by a probe composition of this invention. The regions displaying greatest coloration intensity when subsequently examined under a fluorescence microscope are believed to correspond to chromosomal regions wherein the relative frequency of occurrence of DNA segments occurring in the probe composition is greater than at locations where the coloration is weakest. A starting total genomic DNA with a skewed distribution of DNA segments compared to a normal or naturally occurring distribution of DNA segments in a total genomic DNA can be used to produce probe compositions of the invention that are to be employed for specialized diagnostic purposes, or for test or evaluation purposes, if desired.

For purposes of accomplishing counterstaining in accord with this invention of the human genome by an in situ hybridization procedure, one presently preferred starting total genomic DNA comprises human placental DNA. Such DNA when fragmented and labeled as taught herein to produce probe compositions of the invention, and then used under hybridizing conditions to genomically counterstain a target, produces stained target bodies which are substantially completely identified with minimal variations in coloration intensities. Placental DNA is available from commercial sources, such as Sigma Chemical Company (St. Louis, Mo.).

An example of a useful starting total genomic DNA with apparently a skewed distribution of sequence occurrence in its multiplicity of DNA segments relative to the normal sequence distribution found in the human genome comprises a DNA composition which is representative of the total human genome, but which is enriched in its content of the commonly occurring DNA repeated sequences that occur in the human genome. A product probe composition of this invention containing and based upon such a DNA segment mixture is still characteristically substantially completely hybridizable with the human genome. Such a starting total genomic DNA is exemplified by Cot-1 DNA which is obtainable as catalog #52795A from Life Technologies, Inc., Gaithersburg, Md. Cot-1 DNA is reportedly prepared by the following procedure: Mechanically sheared total human genomic DNA is fragmented to an average sequence size of less than 400 bp. This material is denatured, and then hybridized for a period sufficient to render large fractions of the highly repeated DNA sequences thereof double-stranded. The mixture of double and single-stranded DNA species are then treated (digested) with nuclease S1, a nuclease which specifically degrades single stranded DNA to mono- and oligo-nucleotides. Undigested double-stranded Cot-1 DNA is recovered from this mixture. Cot-1 DNA is reportedly in the form of segments having an average size of about 191 bp.

Thus, such a useful starting total genomic DNA class is derived from a total genomic DNA, denatured, partially reannealed or re-hybridized, and treated with enzymes to reduce the amount of non-repeated segments therein, by processes known to the prior art.

Another example of a suitable starting total genomic DNA is a cloned library of total human genomic DNA, or a set of cloned DNA fragments, which taken together reasonably represent the entire human genome. Libraries of the human genome are available from a plurality of sources. For example, such libraries can be obtained from Stratagene, Inc. (La Jolla, Calif.) either in lambda DNA or cosmid vectors. The source of the total genomic DNA, in the case of pre-made human DNA libraries, can be circulating lymphocytes, lung fibroblasts, placental DNA, or the like. Pre-made libraries prepared from genomes of non-human animal species are also available from this company, as are custom preparations of total genomic DNA libraries that are derived from tissues and organisms. Those skilled in the art will appreciate that the starting total genomic DNA and the product probe composition made therewith can be used in various analytical procedures which follow a hybridization procedure, including subsequent microscopic examination, flow cytometry, or the like.

Both Cot-1 DNA (and similarly prepared materials) and human library DNA typically result in direct label probe compositions of the invention which, when hybridized to the human genome (that is, the individual chromosomes) produce hybrids that give the appearance of substantially complete staining of the target although the hybridized target bodies individually may show relatively strong variations in fluorescent stain intensity.

The nature, structure and size of individual starting DNA sequences, the number of the different sequences utilized, and the like variables associated with a starting total genomic DNA cannot be stated in absolute terms because of inherent variations in the genome from one organism to another, and because the composition of a starting DNA sequence or segment population for a given genome can vary from one source to another, and even from one batch to another of total genomic DNA taken from the same source. However, after fragmentation of a starting DNA sequence, achieved as hereinbelow described, the starting total genomic DNA should produce a mixture of DNA segments which is approximately and reasonably representative of the entire genome involved and wherein individual segments exist which are complementary to segmented regions that occur or are located generally in all regions of the genome.

The characteristic complexity of the starting total genomic DNA from a given genome, however, is presently considered to be desirable from the standpoint of the present invention since such complexity tends to make possible direct label probe compositions of the invention that are prepared as taught herein from different starting total genomic DNA batches obtained from the same organism species behave in a substantially identical manner as regards counterstaining capacity. The high complexity of total genomic DNA distinguishes it, for example, from a less complex DNA such as is present, for instance, in a probe composition which is adapted (because of its DNA content), to hybridize only with a portion of a multichromosomal genome, such as single chromosome (i.e., a paint probe), or a single region of a single chromosome, such as the centromere region. Characteristically, and as is true of genomic DNA generally, a starting total genomic DNA is believed characteristically to contain about 25 mole percent deoxycytidine nucleotides of the total number of deoxynucleotides present therein.

(2) The Starting Linking Compound

A starting linking compound employed in the practice of this invention is a difunctional organic compound, that is, such contains two substituent functional (i.e., reactive) substituents per starting linking compound molecule.

At least one of such functional substituents per linking compound molecule is reactive with deoxycytidine nucleotides in a polynucleotide under bisulfite catalyzed aqueous transamination conditions (such as provided herein, for example). Examples of such substituents include alkyl amino (primary and secondary) hydrazido, semicarbazido, thiosemicarbazido, and the like. Amino groups are presently most preferred.

When the amino group is secondary, the secondary substituent is preferably a lower alkyl group, but other non-blocking such secondary substituents can be used, if desired.

The second of other of such two functional substituents per linking compound molecule is reactive with a third functional substituent which is itself incorporated into a starting fluorescent compound (as herein described). Such second functional substituent can itself be either blocked or unblocked. When the second substituent is unblocked, then it is substantially non-reactive with other substances that are present in the transamination medium (especially polynucleotides) during transamination. When the second substituent is blocked then it is substantially non-reactive with the other substances that are present in the transamination medium (especially polynucleotides) during transamination.

Examples of suitable unblocked second functional substituent group include amino, carboxyl, phosphate, sulfonate, hydroxyl, hydrazido, semicarbazido, thiosemicarbazido and the like. Presently, most preferred unblocked second functional substituent include amino (primary or secondary) and carboxyl groups.

The carboxyl group preferably is either in the salt form or in the acid form, but can sometimes be in the ester form. When in the salt form, presently preferred cations are alkali metals, such as sodium and potassium.

Examples of suitable blocked second functional substituent group include blocked sulfonate, blocked phosphate, blocked sulfhydryl, and the like.

Examples of suitable blocking substituents include lower alkyl groups such as methyl, ethyl, propyl, etc.

The first and the second functional substituents are interconnected together through a linker (or linking) moiety. This linking moiety can have any convenient structure but such is non-reactive with other substances that are present in the transamination medium during transamination. A present preference is that the linking moiety be a hydrocarbonaceous divalent group which is acyclic or cyclical and which can optionally incorporate other atoms.

The two functional substituents present in such a difunctional linking compound can be respective substituents of the linking moiety. Such substituents can be on adjacent carbon atoms relative to each other, or they can be spaced from one another in a linking compound molecule by a plurality of intervening interconnected atoms (preferably carbon atoms). Preferably these functional groups are in an alpha, omega relationship to one another (that is, each is at a different opposite end region) in a given linking compound molecule.

Thus, the two functional radicals in a linking compound are each bonded to an organic linking group moiety which is either entirely hydrocarbonaceous (that is, composed only of carbon and hydrogen atoms), or is comprised of carbon and hydrogen atoms plus at least one additional atom or group which contains at least one atom selected from the group consisting of oxygen, sulfur, nitrogen, phosphorous, or the like. Preferably such additional atom(s) are so associated with such organic moiety as to be substantially less reactive than either one of such above indicated two functional radicals that are present in a given starting linking compound. Hydrocarbonaceous organic moieties that are saturated aliphatic are presently preferred, and more preferably such moiety is a divalent alkylene radical containing from 2 through 12 carbon atoms, inclusive. However, if desired, such a saturated aliphatic radical can incorporate either at least one ether group (—O—) or at least one thio-ether group (—S—), but it is presently more preferred that only one of such ether or thio ether groups be present. It is presently preferred that a linking compound incorporates an organic radical that contains at least two and not more than about a total of about 20 carbon atoms, although more carbon atoms per molecule can be present, if desired.

Presently preferred are linking compounds in which each of such functional radicals is an amino radical. Both acyclic and cyclic diamino compounds can be used.

Examples of suitable aliphatic primary diamines include alkylene primary amines wherein the alkylene group is propylene, butylene, pentylene, hexylene, nonylene, and the like.

Examples of suitable aliphatic secondary diamines include $CH_3NH(CH_2)_2NH_2$, $CH_3NH(CH_2)_2NHCH_3$, and the like.

Diamino compounds incorporating hydroxylated hydrocarbons can be used. Examples of acyclic such compounds include 1,3-diamino-2-hydroxypropane; 1,4-diamino-2,3 dihydroxybutane; 1,5-diamino-2,3,4-trihydroxypentane; 1,6-diamino-1,6-dideoxy-D-mannitol (or D-glucitol or D-galactitol), 1,6-diamino-2,3,4,5-tetrahydroxyhexane, and the like.

Examples of suitable polyhydroxylated cyclic dimensions include cis or trans cyclic diamino compounds where the diamines are constrained in a ring, such as 1,4-diamino-2,3,5,6-tetrahydroxy cyclohexane, cis and trans 1,2-diaminocyclohexane, cis and trans 1,2-diaminocyclopentane, and hydroxylated derivatives thereof, such as 1,2-diamino-3,4,5,6-tetrahydroxycyclohexane, 1,2-diamino-3,4,5-trihydroxy cyclopentane, 3,6-diamino-3,6-dideoxy-derivatives of myo-inositol, such as

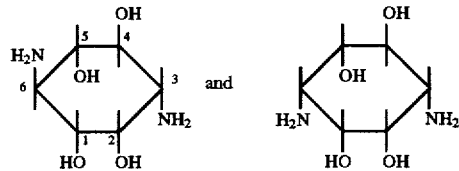

and the like.

Examples of suitable heterocyclic diamines include piperazine, N,N'-bis (3-aminopropyl) piperazine, derivatives thereof, and the like.

Examples of suitable ether-group containing diamines include 3-oxo-1,5-pentanediamine, 3,6-dioxo-1,8-diaminooctane, and the like.

Examples of suitable linking compounds containing both an amino radical and a carboxyl radical include amino acids, such as sarcosine (N-methylglycine), and alpha amino acids, such as glycine, alanine, glutaric acid, aspartic acid, proline, pipecolinic acid (piperidine-2-carboxylic acid), isopipecolinic acid (piperidine-4-carboxylic acid), glucosaminic acid and derivatives thereof, and the like.

Examples of alpha, omega aminocarboxylic acids (in addition to the above identified amino acids) include 4-aminobutyric acid, 6-aminohexanoic acid, 8-aminooctanoic acid, and the like.

Examples of phosphorous containing difunctional linking compounds include alpha, omega aminoalkyl phosphoric acid, monoesters, such as 0-(2-aminoethyl) phosphate disodium salt and the like.

Examples of suitable sulfur containing difunctional linking compounds include alpha, omega aminoalkyl sulfonic acids, such as taurine (2-aminoethyl sulfonic acid) and the like.

One presently more preferred class of difunctional linking compounds is represented by the following generic formula:

wherein

X is a divalent radical selected from the class consisting of:

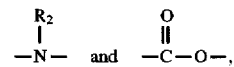

wherein:

R is an alkylene radical containing from 2 through 12 carbon atoms inclusive or per hydroxylated carbocyclic ring and $R_1$ and $R_2$ are each independently selected from the class consisting of hydrogen and lower alkyl.

Preferably, in Formula (1), R contains not more than 7 carbon atoms, X is

and $R_1$ and $R_2$ are each hydrogen, and R contains less than 7 carbon atoms.

Mixtures of different linking compounds can be used, such as linking compounds containing a mixture of mono and/or deamines, but such mixtures are not preferred because of associated problems in transamination control and usage.

Diamines which are characterized by having a large proportion thereof that exists as a free unprotonated species at pH values of about 7 appear to enhance the present transamination reaction. Ethylene diamine (pK of about 7.6) is presently most preferred for use as the reactive difunctional amine because of this property.

When, for example, such a linking compound is bonded to a DNA sequence using a transamination reaction, as hereinbelow described, the transamination reaction is carried out so that an amino radical in the linking compound bonds to the sequence or segment. Then, in the resulting linking group, one functional group remains free to undergo further reaction. Thus, when the second functional radical is an amino radical, such radical remains free thereafter to undergo further reaction with the fluorescent compound, as hereinbelow described. When the second functional radical is a carboxyl radical, such radical remains free thereafter to undergo such a further reaction with the fluorescent compound, as hereinbelow described.

(3) The Starting Fluorescent Compound

The starting fluorescent compounds employed in the practice of this invention each incorporate at least one fluorophore substituent (or group) per molecule and also one functional (i.e., reactive) substituent (or group) per molecule.

The functional substituent is chosen so as to be reactive with the second functional substituent remaining incorporated into a linking group in a transaminated polynucleotide (such as is prepared as described herein.) The linking group is derived from a linking compound (as above described).

For example, in a starting fluorescent compound, the reactive substituent can be chosen to be reactive with an amino substituent (as above defined), or with a carboxyl substituent which is in the acid or the salt form (as above defined).

For purposes of reactivity with such an amino substituent in a linking group (using a reaction as hereinbelow described), the reactive substituent of the fluorescent compound can be a convenient amine-reactive functionality, such as a carboxyl substituent that is in the acid or salt form (such as above defined), an aldehyde radical or the like. A presently preferred such reactive substituent is selected from, and exemplified by, the group consisting of isothiocyanates, N-hydroxysuccinimide esters, sulfonyl chlorides, carboxylic acid azides and the like.

For purposes of reactivity with such a carboxyl substituent in a linking group, the reactive substituent of the fluorescent compound can be a convenient carboxyl-reactive functionality, such as an amino substituent which is in a primary or a secondary form (such as above defined) or the like. A presently preferred such reactive substituent is a primary amino substituent.

The reactive substituent can also sometimes be, for example, a thiol, a phosphate ester, or the like, the choice, depending upon the nature of the reaction substituent that is present in a linking group.

In general, any fluorophore substituent or group can be employed in a starting fluorescent compound. If more than one fluorophore substituent per fluorescent compound is used, then it is presently preferred that each fluorophore substituent be similar or identical in structure to others thereof in a single fluorescent compound. A present preference is to employ fluorescent compounds containing about 1 to about 3 fluorophore substituents per fluorescent compound molecule and most preferably a fluorescent compound contains only one fluorophore substituent per fluorescent compound molecule.

Preferably, a starting fluorescent compound has a molecular weight which is not more than about 5000 and more preferably not more than about 1000 because larger molecular weights may possibly have an adverse effect upon the hybridization capacity of a product probe with a complementary target sequence.

For reasons of detectability, it is presently preferred that a starting fluorescent compound and the fluorophore groups therein have an extinction coefficient of at least about 6,000$M^{-1}$ cm$^{-1}$ (and preferably at least about 10,000$M^{-1}$ cm$^{-1}$) in the wavelength region of the excitation light incident on a given specimen, and also a quantum yield of at least about 0.02. The term "extinction coefficient" is used herein in its conventional sense to mean the absorbance of a 1 molar (M) solution of the fluorescent compound contained in a 1 centimeter (cm) path length cuvette. Similarly, the term "quantum yield" is used herein in its conventional sense to mean the number of photons emitted by a fluorophore per the number of photons absorbed by that fluorophore.

Exemplary and presently preferred starting fluorescent compounds are shown in Table I below.

TABLE I

EXEMPLARY STARTING FLUORESCENT COMPOUNDS[1]

1. 7-amino-4-methylcoumarin-3-acetic acid, succinimidyl ester (AMCA)
2. sulforhodamine 101 sulfonyl chloride; also known by the name Texas Red ™ or Texas Reo ™ sulfonyl chloride (Tx Rd)
3. 5-(and-6)-carboxyrhodamine 101, succinimidyl ester; also known by the name 5-(and-6)-carboxy-X-rhodamine, succinimidyl ester (CXR)[2]
4. Lissamine rhodamine B sulfonyl Chloride (LisR)
5. 5-(and-6)-carboxyfluorescien, succinimidyl ester (CFl)[2]

TABLE I-continued

EXEMPLARY STARTING FLUORESCENT COMPOUNDS[1]

6. fluuorescein-5-isothiocyanate (FITC)[2]
7. 7-diethylaminocoumarin-3-carboxylic acid, succinimidyl ester (DECCA)
8. tetramethylrhodamine-5-(and-6)-isothiocyanate (TRITC)[2]
9. 5-(and-6)-carboxytetramethylrhodamine, succinimidyl ester (CTMR)[2]
10. 7-hydroxycoumarin-3-carboxylic acid, succinimidyl ester (HCCA)
11. 6-[fluorescein-5-(and-6)-carboxamido]hexanoic acid (FCHA)[2]
12. N-(4,4-difluoro-5,7-dimethyl-4-bora-3a,4a-diaza-3-indacenepropionic acid, succinimidyl ester; also known by the name 4,7-dimethylSODIPY ™ propionic acid, succinimidyl ester (DMVP)
13. "activated fluorescein derivative" (FAP); this compound consists of a fluorescein nucleus connected through a spacer group to an N-hydroxysuccinimide ester reactive group and designated as "FAP" by the manufacture, Molecular Probes, Inc.
14. eosin-5-isothiocyanate (EITC)[2]
15. erythrosin-5-isothiocyanate (ErITC)[2]
16. Cascade ™ Blue acetylazide (CEAA); which is the O-acdetylazide derivative of 1-hydroxy-3,6,8-pyrenetrisulfonic acid

[1]Abbreviations used to refer to these compounds are enclosed within parentheses. For some coumpounds alternative names, including trademarked names, are provided. ™ refers to trademarks of Molecular Probes, Inc. The term "succinimidyl ester" refers to the ester formed between a carboxylic acid substituent of the fluorophore and N-hydroxysuccinimide, and is also referred to as an "N-hydroxysuccinimide ester" or an "N-hydroxysuccinimidyl ester" or an "NHS ester".
[2]certain fluorescein and rhodamine derivatives contain reactive substituents (carboxy or isothiocyanate) attached to eitehr the 4- or 6- positions. These compounds can be obtained as mixtures of the two isomers, designated as "5-(and-6)-", or in some cases as the purified isomers. The labeling and fluorescent properties are not expected to vary greatly between isomers or between a specific isomer and the mixture. The isomers or mixtures designated above were those used in labeling experiments (see Examples).

All fluorescent compounds in Table I were obtained from Molecular Probes, Inc. Eugene, Oreg.

As those skilled in the art will readily appreciate, a starting fluorescent compound is preferably selected for use in making a given product probe composition which will produce, under conditions of fluorophore excitement in a single specimen, emitted light of a color which contrasts with the color of the light emitted by the fluorophore group-containing label portion of any concurrently or sequentially used other probe or probe composition which is targeted to the same or related karyotype, such as a genome, a specific chromosome, or a specific region of a chromosome, or the like that is within the genome involved.

(C) Probe Production (General)

Primarily because of their characteristically relatively large typical size, as above indicated herein, starting total genomic DNA sequences apparently tend to display relatively poor hybrid forming capacity (after being labeled).

Also, previously known prior art chemical synthetic methods for joining label moieties to a nucleotide sequence, particularly a fluorophore-containing label moiety, tend to result in problems of controlling the location and the number of label moieties per sequence, and also in problems of sequence alteration. These problems can adversely affect the resulting probe hybridization capacity with the desired genomic target materials, and also, ultimately, the detection by counterstaining of total genomic DNA present in a specimen.

It has now been discovered that these problems can be overcome, and that a direct label probe composition of excellent hybrid forming capacity and probe performance characteristics for genomic counterstaining purposes in in situ hybridization exists, when a probe composition is comprised of a mixture of genomically derived DNA segments such as is described herein wherein the segments are chemically bound to fluorophore groups through linking groups.

Various procedures can be employed to prepare such a probe composition. A presently preferred and illustrative preparation procedure is now described in which the following procedural steps are carried out:

(a) Fragmenting (i.e., disrupting) DNA sequences comprising a total genomic DNA into DNA fragments (or segments);

(b) Transaminating deoxycytidine nucleotides existing in the sequences (and consequently also in the derived segments) with a linking compound (as above described); and (c) Covalently bonding residual radicals of the so produced transaminated linking groups with a fluorescent compound (as above described).

While step (b), or step (b) and (c), can precede step (a), it is presently preferred for step (a) to precede step (b). In the following description, the foregoing (a), (b), (c) step sequence order is used for present organization purposes.

Other combinations and variations of such step sequences are also feasible for use in preparing a probe composition of this invention. For example, one can covalently bond the fluorescent compound to the linking compound, then transaminate and finally fragment the DNA sequences (using step conditions similar to those herein provided); however, this procedure tends to result in low yields due to the lower solubility of the fluorophore group in the transamination reaction.

(2) Fragmenting

The DNA segments are derived from a starting total genomic DNA (as above characterized). Before fragmenting, the starting DNA preferably has average sizes of at least about 150 bp. After fragmenting, the DNA segments preferably have an average size that is within a range of about 150 to about 600 bp with a presently more preferred average size being about 180 to about 400 bp, and a presently most preferred average segment size being about 300 bp. Each of these segment fragments is believed to be complementary to a segmental portion existing in one or more DNA sequences which occur in one or more chromosomes of the genome from which such segment fragments were derived.

The number of fragments derived from starting genomic DNA sequences in any given instance is unknown, probably variable from one batch to another, and large. Also, the structure of the nucleotide sequences of the individual fragments is unknown and probably variable from one batch to another. It is presently estimated that the number of starting fragments that are formed from given starting total genomic DNA sequences in any given instance is at a minimum in the thousands. For reasons associated with the capacity of a product probe composition to counterstain genomic DNA and the brightness of the fluorescence in hybrids formed therewith, it is presently believed to be desirable to utilize DNA fragments having a relatively uniform average size in the ranges above indicated.

As those skilled in the art will readily appreciate, these DNA fragments can be formed from starting genomic sequences by various known techniques, including, for example, enzyme treatment, as with restriction enzymes or polymerases, or the like; limited DNase I digestion; limited mung bean nuclease digestion; sonication; shearing DNA in a French press; shearing DNA through a narrow gauge needle; and the like.

However, it is presently greatly preferred to form such DNA fragments by sonication of a starting total genomic DNA. Sonication can be carried out by any convenient procedure. Presently preferred sonication conditions utilize an aqueous dispersion of starting total genomic DNA that is preferably in the range of about 0.05 to about 4 mg per ml, although smaller and larger such concentrations can be employed. The ultrasonic frequency applied is preferably in the range of about 20,000 cycles per second and is applied for a total time in the range of about 1 to about 10 minutes with the tube containing the sample preferably immersed in a cooled bath to reduce heating of the sample. Suitable cooled baths include ice baths and baths containing dry ice and ethanol. Energy density applied to the DNA sequence material undergoing such ultrasonic processing is variable. For example, in the case of a Branson Sonifier Model 450 (Danbury, Conn.) with the microtip located about 2 to about 5 mm from the bottom of the tube in an aqueous solution, a suitable output power is in the range of about 25 to about 30 watts. Preferably, such ultrasonic energy is applied using about an 80% on time, and, correspondingly, about a 20% off time, for a total time of about 5 minutes, such as below exemplified herein.

Preferably, the starting genomic DNA is fragmented before the sequences are subjected to transamination.

Regardless of the method of fragmenting, the result of fragmenting the plurality of sequences comprising a starting total genomic DNA is to produce a profusion of fragments of such starting DNA sequences. This profusion comprises DNA segments that individually occur at each one of a plurality of different locations or regions in each one of the individual chromosomes comprising the genome used.

The starting DNA sequences (and also consequently the fragmented segments derived therefrom) characteristically are now believed to contain on average at least about 25 mole percent deoxycytidine nucleotides on a 100 mole percent total nucleotide basis.

Obviously, if the starting total genomic DNA is obtained commercially in an already fragmented state, such as is, for example, the case with Cot-1 DNA, then a separate fragmenting step is not needed before a subsequent step, such as transamination is undertaken.

The fragmented DNA segments are thus mixtures that are derived from the total genomic DNA of a given genome and are approximately representative of the segments present in this total genomic DNA. Segment sizes are in the ranges above indicated. Such a DNA segment mixture can be produced by any convenient procedure from DNA sequences comprising the total genomic DNA. The human genome is presently preferred.

Presently preferred individual starting mixtures for making a probe composition of the invention which is useful as a directly detectable genomic DNA counterstain for chromosome detection include:

(a) human placental DNA which has been sonicated and thereby fragmented into DNA segment average sizes between about 150 and about 600 bp (preferably about 200 to about 400 bp).

(b) total human genomic DNA which has been sonicated and/or digested into segment sizes between about 150 and about 600 bp (preferably about 200 to about 400 bp) and which DNA segments have been further subjected to, for example, denaturation, selective re-hybridization and enzymatic digestion using, for example, a technique such as taught herein or in the prior art, thereby to produce a DNA segment mixture which is enriched in repetitive (i.e., repeated) DNA segments compared to the level of such repeated DNA segments which naturally occur in the genome, but which still contains albeit to a lesser than naturally occurring extent, DNA segments that are specific to representative regions or DNA segmental portions occurring throughout the entire genome; and (c) total human genomic DNA which has been fragmented by sonication into segment sizes between about 150 and 600 bp (preferably 200 to about 400 bp) and which DNA has been produced as a cloned genome library from bacteria or the like.

(3) Transamination

In the transamination, a fraction of the total deoxycytidine bases that are contained in the starting genomic DNA sequences and segments thereof become transaminated with an amino group of a difunctional linking compound (as above described) in the carbon 4 (C-4) atom position of the amino group of deoxycytidine nucleotides. The extent of such transamination is such that between about 1 and about 70% of all deoxycytidine nucleotides that are present in a starting mixture of DNA segments that is representative of total genomic DNA of a given genome are thus substituted by such a linking group. Preferably, about 2 to about 24 mole percent of all deoxycytidine nucleotides contained in such a mixture of starting DNA sequences or DNA fragments are thus transaminated. Expressed alternatively, about 0.2 to about 18 mole percent, and preferably about 0.5 to about 6 mole percent, of the total nucleotides present in the DNA fragments or sequences are transaminated. All such transaminations involve substantially only deoxycytidine nucleotides. Most preferably only about 1 to about 5 mole percent of the total nucleotides present are thus so transaminated.

The most effective percentage of transamination in any given instance is typically influenced by the particular fluorescent label moiety used. Since the average number of base pairs present in a sequence is preferably at least about 150, as above indicated, each sequence is thus preferably substituted by at least about one such linking group during the transamination procedure, as desired. Transamination to a greater extent seems to increase the potential of adversely affecting the specifity of product probes (subsequently) labeled with some fluorophores, such as FITC and TXRd, for example. High amination levels do not affect as greatly the specifity of CTMR and DECCA labeled probes, for example. Transamination to a lesser extent seems to adversely affect the brightness of fluorescent light generated in detecting product hybrids.

The transamination is conveniently accomplished under aqueous liquid phase conditions in the presence of a bisulfite catalyst. The concentration of DNA sequences (or segment fragments) is conveniently in the range of about 0.1 to about 1 mg per ml, the concentration of bisulfite anions is conveniently in the range of about 0.5 to about 1.4 moles per l (where "l" means liter), the concentration of linking compound is conveniently in the range of about 1 to about 5 moles per l, the pH is conveniently in the range of about 4.5 to about 8.0, the temperature is conveniently in the range of about 20° to about 45° C., and the contacting time is typically and exemplarily in the range of about 3 to about 72 hours (depending upon the amination level desired).

In the present transamination procedure, the bisulfite is conveniently introduced in the form of an alkali metal salt, with sodium and potassium being preferred alkali metals.

At the time of transamination, the linking compound is dissolved in the aqueous transaminating medium.

During the transamination, the DNA sequences or segments are preferably denatured, for example, by carrying out the transamination in the presence of a chaotrope, or by a preliminary boiling of DNA sequences or segments in water, such as for a time of about 1 to about 10 minutes followed by chilling to a temperature below about 4° C. (presently preferred), or by a combination of both procedures.

The technique and advantages of employing a chaotrope in the transamination are taught in the Bittner et al. copending U.S. patent application Ser. No. 07/762,912, now U.S. Pat. No. 5,506,350 filed on even date herewith and identified by the assignee's Docket No. 30,456, and such teachings are incorporated hereunto by reference.

The complexity of the DNA fragment mixture is illustrated and exemplified by the extent of transamination achieved after denaturing of the DNA fragments by boiling. Since transamination only occurs at an appreciable rate on single stranded DNA, and since the reformation rate slows in proportion to the complexity of the DNA, the total genomic DNA is found to transaminate to a greater extent than is characteristic for relatively somewhat simpler DNA mixtures, such as a DNA mixture which is being aminated to produce a paint probe under the same conditions, as taught in such above-referenced concurrently filed copending Bittner et al. application. Indeed, in the present transamination, use of mild transamination conditions is preferred to avoid over-amination beyond the range above indicated. One adverse effect of over-amination is to reduce the complementary character of the transaminated sequences and segments and the resulting capacity thereof to hybridize to desired complementary target DNA.

During the transamination with the bisulfite catalyst, reaction variables as above identified can be varied within the ranges indicated to achieve a desired degree of transamination with a given linking compound reactant.

The present transamination reaction is carried out or continued until a desired extent of transamination of the starting DNA sequence or segment mixture is obtained. In general, the maximum extent of transamination is determined by the level of transamination which causes, or begins to cause, either an adverse effect upon the complementary character of the nucleotide sequences or segments involved, or an increase in the amount of non-specific association of the subsequently labeled probe with target DNA or other constituents of a target DNA, such as exist in a specimen, slide preparation or the like, during an in situ hybridization using a probe composition of this invention. Even at the relatively low levels of transamination utilized in the practice of this invention, there are evidently typically and preferably present in a transaminated product only a low mole percentage of totally unlabeled DNA sequences. The minimum level of transamination achieved in any given instance is determined by the objective of achieving uniform staining of potentially all chromosomes of the genome should such be present in a given specimen. Even low amination levels do provide such uniformity.

Another factor favoring low levels of transamination is that in practice it is often desirable to have the target portion of the total genomic DNA that is present in a given sample or specimen counterstained only relatively lightly so as not to obscure regional or specific staining achieved, for example, by other probe compositions used in combination with a counterstaining probe composition of this invention.

The intensity of the genomic counterstain achievable in a specimen with a counterstaining probe composition of this invention can be readily regulated or reduced, if desired, so as to achieve a desired background counterstain coloration intensity in a given specimen or the like. Such a reduction can be achieved by various techniques, such as, for example, by lowering the extent of linking group transamination, thereby ultimately diluting the quantity of labeled genomic DNA segments that are present in a counterstaining probe composition of this invention, by diluting a transaminated mixture with a starting DNA segment mixture, or the like.

The fluorescent intensity of labeled probe composition can be reduced by the addition of unlabeled starting total genomic DNA thereto prior to the time when fluorescent compound bonding is performed (as below described).

The minimum level of transamination practiced in any given instance is conveniently determined by the desire to transaminate at least a predetermined mole percentage of the total deoxycytidine nucleotides present in the starting DNA, such as a fragmented DNA segment mixture.

A mixture resulting from a transamination procedure that is in accord with the teachings of the present invention can be conventionally further processed. A present preference is to dialyze such a product mixture, against a dilute aqueous buffer, such as sodium borate, tris(hydroxymethyl) aminomethane (TRIS), or the like at a pH of about 8 using a conventional dialyzing membrane and ambient temperatures.

The resulting mixture of transaminated nucleotide sequences or segments is then conveniently precipitated from the so dialyzed mixture, and the sequence is then separated from the supernatant by filtration, centrifugation, or the like.

(4) Fluorescent Compound Bonding

A resulting transaminated and amine substituted nucleotide derivative is then available for covalently bonding with a reactive fluorophore substituent-containing fluorescent compound, such as above described, with such compound reacting with a terminal functional substituent associated with the residue of the linking compound (i.e., the linking group) that has now been transaminated into a deoxycytidine moiety as above described. The number of fluorophore substituent-containing fluorescent compounds thus reacted per sequence or segment molecule is easily controlled. Preferably, starting DNA sequences are fragmented before being bound to fluorophore groups. Consequently, in a product probe composition, the number of label groups per DNA molecule is regulatable, as desired. The nucleotide sequence of each segment in the resulting product probe composition is believed to be substantially identical to that existing in a starting DNA mixture except for the added presence of the transaminated linking groups and the covalently bonded fluorophore groups.

The covalent linking or bonding of fluorescent compound to a terminal radical of a linking group in, for example, transaminated DNA segments is conveniently carried out under aqueous liquid phase conditions using a temperature in the range of about 4° to about 50° C., a concentration of transaminated DNA in the range of about 10 to about 500 µg per ml, a near-neutral pH for reactions of N-hydroxysuccinimide esters (e.g., pH of about 6 to 8) and an alkaline pH for reactions of isothiocyanates and sulfonic acid chloride (e.g., pH 8.5–9.5) and a time which is typically and exemplarily in the range of about 2 to about 18 hours.

Typically and preferably, the quantity of the starting fluorescent compound present is sufficient to provide a substantial molar excess relative to the total quantity of linking groups that are estimated to be present in the transaminated DNA sequences. In any given situation, an optimized molar excess can be conveniently determined relative to the concentration of the aminated deoxycytidine nucleotide residues present in the fragments.

While theoretically the amount of fluorescent labeling compound only needs to equal the amount of aminated deoxycytidine in the probe DNA, an excess is usually greatly preferred since some of the fluorescent compound molecules react by other routes which do not lead to attachment of label to DNA, such as reaction with water (hydrolysis), thereby to render a labeling compound nonreactive with aliphatic amine groups. Excess labeling compound is also used to increase the rate of reaction with the aminated deoxycytidine so that the reaction is complete in a shorter amount of time. A larger excess is required for labeling compounds more sensitive to hydrolysis, such as N-hydroxysuccinimide esters and sulfonic acid chlorides, relative to compounds less sensitive to hydrolysis such as isothiocyanates. While a small excess of labeling compound to aminated deoxycytidines may lead to low percentages of probe labeling, a large excess of labeling compound can be advantageous in providing high labeling percentages. Labeling compound quantities in excess of that required to achieve complete labeling is not disadvantageous to the labeling reaction. Very high amounts of labeling compound, however, can lead to post-reaction purification problems since substantially all of the unreacted fluorescent compound must be removed prior to using the product probe composition in in situ hybridization or the like. Therefore, very large excesses of fluorescent compounds are to be avoided, such as excesses greater than about a 250 fold molar excess.

When, for example, the fluorescent labeling compound is a succinimidyl derivative (that is, an N-hydroxysuccinimide ester of a carboxyl substituted fluorophore or the like), or a corresponding sulfonic acid chloride derivative, then the transaminated DNA sequences containing the residual linking compound are conveniently reacted with about a 100 to about a 200 fold molar excess of the fluorescent labeling compound, a present preference being about a 150-fold molar excess.

When, for example, the fluorescent labeling compound is an isothiocyanate derivative, then the transaminated DNA sequences are conveniently reacted with about a 50-fold molar excess of the fluorescent labeling compound.

In the reaction which occurs, covalent bonding is believed to occur between the reactive group of a starting fluorescent compound and the terminal group of a transaminated linking group (derived from a linking compound) that is associated with a DNA sequence. Preferably, at least one terminal group of one linking group per molecule is reacted with the fluorescent compound employed. Typically, about 10 to about 100 mole percent of the terminal sites of the linking groups are reacted and thus fluorescently labeled. Preferably, for efficiency reasons, at least about 70 mole percent thereof are so labeled, and most preferably about 90 mole percent thereof are so labeled.

Residual labeling compound not covalently attached to the probes at the end of the reaction time can be removed by a variety of methods, such as precipitation of the DNA, gel permeation chromatography, affinity chromatography, dialysis, gel electrophoresis, and combinations of these methods. The number and types of procedures combined to purify labeled probes depends upon the size of the labeling compound, including the size of aggregates of these labeling compounds, and their ability to noncovalently bond with the labeled DNA, such as through ionic and hydrophobic interactions. One procedure which provides adequate removal of unreacted labeling compound involves an ethanol precipitation step followed by a gel permeation chromatography step followed by a second ethanol precipitation step. The resulting precipitated labeled probe can be dissolved in water to provide a stock solution of probe which may be used directly in in situ hybridization reactions when combined with the other hybridization components (e.g., formamide, dextran sulfate, buffer, and specific probe compositions).

The resulting reaction product of the transaminated DNA sequences and the selected fluorescent compound comprises a probe composition of this invention.

(5) Direct Label Probe Compositions

Thus, there is provided a direct label probe composition wherein DNA segments are bound to fluorophore groups. Such probe composition is suitable for use in genomic DNA counterstaining and for detecting by in situ hybridization or the like the presence in a specimen containing target genomic DNA of a chosen multichromosomal genome. Such a probe composition contains a plurality of different DNA segments occurring throughout each one of the genome's component chromosomes that individually occur at each of a plurality of locations. These DNA segments are substituted on about 1 to about 70 mole percent of the total deoxycytidine nucleotides thereof with a linking group structure which retains a terminal functional (or reactive) group. At least about 10 mole percent of all such retained terminal functional groups have each been covalently bound to an individual group which incorporates a fluorophore substituent. Individual ones of such so labeled plurality of DNA segments that thus comprise a probe composition of this invention are hybridizable to complementary DNA segments found in regions occurring in each one of a plurality of locations existing throughout DNA of the chosen genome.

Preferably, in a probe composition of this invention, this difunctional linking group is characterized by the formula:

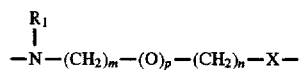

wherein:

X is selected from the divalent group consisting of:

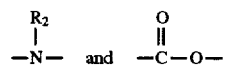

$R_1$ and $R_2$ are each independently selected from the group consisting of hydrogen and lower alkyl;

m and n are each an independently selected integer of 1 through 6 inclusive; and p is the integer 0 or 1, and wherein the group:

is transaminated to a deoxycytidine nucleotide of one said DNA sequence and the group —X— is covalently bonded to one said label moiety.

Thus, a direct label probe composition of this invention comprises a mixture of DNA segments which are derived from, and are approximately a representation of, the total genomic DNA of a given genome. A presently preferred genome is the human genome. These DNA segments are chemically bound through the intervening linking groups to fluorophore groups. The characteristics of probe compositions of this invention are summarized for convenience in Table II below:

TABLE II

Characteristics of Probe Compositions of the Invention

| | Ranges (approximate) | | |
|---|---|---|---|
| Variable | Broad | Preferred | Presently Most Preferred |
| 1. Mixture of DNA Segments | | | |
| 1.1 Individual segment average size in bp | 150–600 | 200–400 | about ~300 |
| 1.2 Mole percent of all deoxycytidines in DNA segments substituted by linking group | 1–70 | 2–24 | 4–20 |
| 2. Difunctional linking group | | | |
| 2.1 No. of carbon atoms per group | 2–20 | 2–6 | 2 |
| 2.2 No. of linking groups per DNA fluorophore group | 0.4–100 | 1–24 | 3–15 |
| 3.2 Mole percent of all linking groups substituted by fluorophore group | 10–100 | 70–100 | 90–100 |
| 3.3 No. of fluorophore per segment | 0.04–1000 | 0.7–24 | 2.7–15 |

The probe compositions of this invention can be utilized, that is, made, sold, and used in various forms, including dry solid (particularly particulate) form, aqueous solutions, and aqueous formulations that are adapted for direct usage in a hybridization procedure.

In aqueous media, a probe composition of the invention is preferably in a substantially completely dissolved form. As those skilled in the art of DNA probes will appreciate, the content of an aqueous formulation of a probe composition (including a hybridization solution) can vary widely depending upon many variables and objectives. For an illustrative example, one suitable class of hybridization solutions has a composition as characterized in Table III below:

TABLE III

Illustrative Class of Probe Composition Suitable For Use in In Situ Hybridization

| | Ranges (approximate) | |
|---|---|---|
| Component | Broad | Preferred |
| 1. Probe Composition of the Invention | 1–200 ng/µl | 5–60 ng/µl |
| 2. Denaturant | 0–80% (v/v) | 50–80% (v/v) |
| 3. Hybridization Rate Promoter | 0–15% (w/v) | 8–12% (w/v) |
| 4. Buffer Salt(s) | 5–100 mM | 10–50 mM |
| 5. Hybrid Stabilizer salt | 0.05M–1M | 0.2 . 0.5M |
| 6. Blocking DNA | 0–1 µg/µl | 0.1–0.3 µg Cot-1 DNA/µl 0.2–0.7 µg human placental DNA/µl |
| 7. Water | Balance | Balance |

In such a probe composition of Table III, the denaturant functions to promote denaturization of the DNA segments present in a probe composition. Such promoted denaturation is desirable because it lowers the temperature employed for denaturation and for hybridization. While the various denaturants known to the prior art can be employed, a presently most preferred denaturant is formamide.

Similarly, the various hybridization rate promoters known to the prior art can be used. A presently most preferred hybridization rate promoter is a dextran sulfate.

Similarly, the various water soluble buffer salts known to the prior art can be used. A present preference is to maintain the pH of a probe composition solution at a value that is in the range of about 5.5 to about 8.5. Buffer salts which are suitable for maintaining such a pH include, for example, citric acid, tris (hydroxymethyl) amino methane, phosphoric acid, and the like. A presently preferred buffer salt composition can comprise citric acid (or sodium citrate).

Similarly, a hybrid stabilizer salt which promotes stabilization of hybrids formed during a hybridization procedure is desirable. The hybrid stabilizer salts known to the prior art can be used, such as NaCl, KCl, $MgCl_2$, and the like. However, the presently most preferred such salt is sodium chloride.

The water used is preferably preliminarily distilled or deionized.

An optional but preferred component of a probe composition of Table III is a blocking DNA composition.

The use of a diluent DNA in the manufacture of a probe composition of the invention is above discussed (see the above subsection on transamination) as one means for regulating fluorescent intensity in a hybridized target. A diluent DNA can also function as a blocking DNA composition and as a means for regulating fluorescent intensity and hybridizing specificity. Presently a preferred blocking DNA composition for blocked probe compositions of this invention which are targeted in the human genome or chromosomes thereof include fragmented human placental DNA and Cot-1.

A blocking DNA composition is beneficial when specific probe preparations are being used in combination with the labeled genomic probe compositions of this invention since repetitive sequences in the specific probe preparation will be prevented from hybridizing to the same repetitive sequence in non-targeted chromosomes. Such a hybridization also occurs when the blocking DNA composition is present at the time when a probe composition of this invention is being hybridized under hybridizing conditions with a target. The hybridization of blocking DNA composition DNA segments to target complementary segmental regions also occurs. The effect of such hybridizations is to regulate the intensity of the fluorescence produced by a given probe composition after hybridization to a target composition. The quantity of blocking DNA composition present is now believed to be inversely related to the hybrid intensity observed after hybridization; however, there appear to be many variables influencing the relationship. A resulting mixture of a probe composition of this invention and a blocking DNA composition can optionally be subjected to hybridizing conditions for a period of time before being subsequently used for hybridization with a target. Alternatively, one can use a denatured blocked probe composition for hybridization with a target under hybridizing conditions.

The compositions of Table III can be prepared from preliminarily prepared precursor compositions which are admixed together at the time of usage in a hybridization procedure. Such precursor compositions can be referred to as a "kit".

An analysis of how and why a probe composition is able to function as a genomic counterstain is now provided as a theory, and there is no intent herein to be bound thereby:

Light emitted from different points within a specimen, observed using a light microscope, must be separated by greater than the diffraction limit in order for the points to be distinguished separately. The diffraction limit is about 0.4 µm for visible light with a wavelength of 500 nm. If points of fluorescent emission are closer together, they will appear as a single point. This information may be used to approximate the fraction of the total genomic DNA probe segments which must hybridize to chromosomes in order to provide what appears, under microscopic examination, to be substantially complete coverage. Complete coverage or staining can thus be considered to be a theoretical condition in which probes have hybridized to target DNA in such a way that the fluorophore group of each resulting hybrid is located no further than about 0.4 µm from one another adjacent such group.

This situation is theoretically, diagrammatically and illustratively shown in FIG. 1 for a single metaphase chromosome 30 containing sister chromatids 31 and 32, where each individual hybridized probe (or hybrid site) is represented by a dot 33. For simplicity, the depth of field is assumed to be large enough that the entire depth of the chromosome 30 is visible to the viewer and the chromosome 30 can be considered to be two-dimensional. The theoretical number of hybridized probes required for substantially complete coverage of chromosome 30 is about 7.2 probes/µm².

Figure 2:
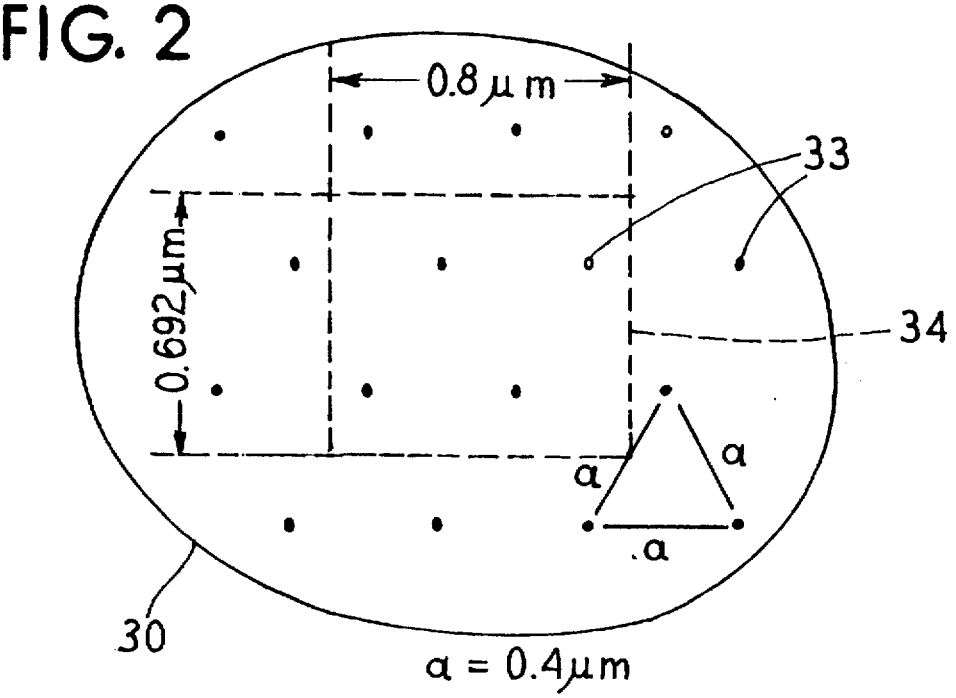
FIG. 2 is a diagrammatic, greatly enlarged theoretical view of a region of the chromosome of FIG. 1.

This situation is further illustrated in FIG. 2, which shows a theoretical extended region of chromosome 30 and dots 33. Each dot 33 is separated from others by 0.4 µm, and a subregion containing four dots 33 (or probes) is outlined with a dotted square 34 which square 34 has the dimensions 0.692 µm×0.800 µm, therefore providing 4 dots per 0.554 µm² or 7.2 dots/µm².

The density of base pairs within individual chromosomes can be approximated from the approximate average two-dimensional size of a chromatid when viewing metaphase chromosomes under the microscope. An average chromatid length is here taken to be about 3 µm and the average width is here taken to be about 0.5 µm, giving an area of about 1.5 µm²/chromatid. Since there are 92 chromatids (4 per chromosome pair) in a normal set of human metaphase chromosomes), the total chromosomal area is 138 µm². Since there are about $3 \times {}^9$ base pairs per haploid human genome, and since there is about 4 times this number in a metaphase nucleus, the base pair density is about $8.7 \times 10^7$ base pairs per µm². Given a minimal probe density of 7.2 probes/µm² for substantially complete coverage of the chromosomes and an average size of about 300 base pairs per probe, a minimum of 1 base pair of probe must be hybridized per 40,000 base pairs of chromosome. When a probe composition is prepared from total genomic DNA, such as the total DNA isolated from human tissue (e.g. human placenta), then only about 0.0025% of the segments contained within a probe composition need to hybridize to the chromosomes to provide substantially complete coverage (which is equivalent to about 0.0025% of all the human chromosomes being hybridized to a probe composition of the invention), assuming all regions of the chromosomes are about equally accessible to hybridization.

Visual detection of a single fluorescent spot, observed, for example, on a chromosome under the microscope, requires the presence of a plurality of fluorophore radicals or labels. This number is now theoretically estimated to be about 300 to about 3,000 fluorescent labels (i.e., fluorophore radicals). Visibility is influenced by the equipment being used for target hybrid examination and the sensitivity of the sensor, such as the human eye, or a photosensitive detector. Using DNA probes having an average length of about 300 base pairs that are aminated and labeled with fluorophore at a level of about 1% (that is, 1 fluorophore group directly-attached to about 1 in 100 bases, or about 3 fluorophore groups per probe) such as taught herein, a microscopically visible fluorescent spot should contain between about 100 and about 1,000 hybridized probes. For substantially complete coverage, as described in the preceding paragraph, this estimate corresponds to about 720 to about 7,200 probes/$\mu m^2$ or about 1 base pair probe per 400 to 40 base pairs of a chromosome. This means that between about 0.25% to about 2.5% of the total number of different segmental regions present within a human total genomic probe preparation must hybridize to the human chromosomes to provide capability for visual detection of completely stained chromosomes (which is equivalent to about 0.25 to about 2.5% of the chromosomal DNA being hybridized to a probe composition).

The preceding theoretical calculations illustrate and support the practically observed result that only a surprisingly small portion of all the human chromosomes need to be hybridized with a probe composition to provide substantially complete and visually detectable staining thereof.

Also, such calculations illustrate a possible basis for the observed result of achieving both a substantially complete counterstaining of given total genomic DNA by a probe composition of this invention and also a coexisting staining of, for example, specific chromosome regions present in such given genomic DNA by a chromosomal region-specific probe composition. Thus, both all the human chromosomes as well as specific subsets or regions thereof can be simultaneously and separately stained in a given target specimen.

In fact, and for example, substantially complete staining of all human chromosomes in a target specimen is achieved when a direct-fluorophore-labeled probe composition of this invention is prepared from the total DNA extracted from human placental tissue. Thus, for example, a direct-fluorophore-labeled probe composition was prepared, for example, from a cosmid library constructed from total human DNA extracted from human placental tissue, such as a pWE15 Cosmid library, (available from Stratagene Cloning Systems, La Jolla, Calif.) and substantially complete staining (hybridization) of all human chromosomes was achieved therewith. Library construction, however, does not insure that all the DNA segments present in the original placental DNA become inserted within the cosmid vectors. Metaphase chromosomes, stained with a probe composition prepared from the cosmid library typically show substantially complete staining which in individual chromosomes is not equal in intensity from one hybrid (or fluorophore) location to another. Bands of brighter and lighter staining alternating down the lengths of the individual chromosomes are observed. The probe composition is still useful, however, as a genomic counterstain since all the chromosomes are substantially completely stained. A mottled appearing staining of the individual chromosomes is sufficient to identify substantially completely the body of each chromosome.

Direct fluorophore-labeled probe compositions of the invention wherein the DNA segments result from treating total genomic DNA with enzymes to remove non-repetitive sequences (such as, for example, Cot-1 DNA from Life Technologies, Inc., Bethesda, Md.) are also useful for counterstaining. Although total genomic DNA treated with enzymes reduces the amount of some genomic sequences, nevertheless, metaphase chromosomes stained with (i.e., hybridized with) a probe composition made from such a total genomic DNA shows both staining across the length of all the chromosomes, as well as brightly stained regions of chromosomes and lightly stained regions of chromosomes. However, all of the chromosomes so hybridized were counterstained to some extent, making the stain achieved, in effect, substantially complete.

Figure 3:
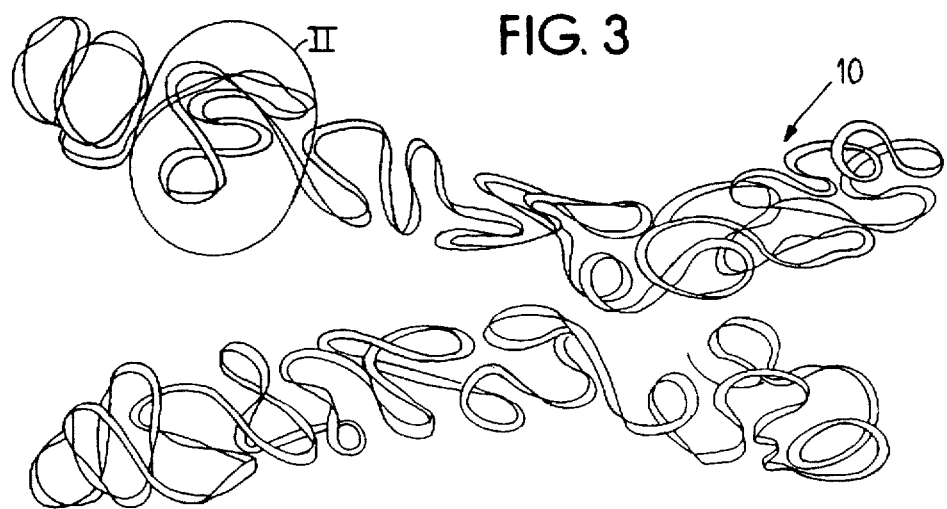
FIG. 3 is a diagrammatic microscopic view illustrating a single mammalian-type chromosome.

Genomic counterstaining capacity of a probe composition of this invention is further illustrated by reference to FIGS. 3–6. The theoretical appearance of an individual chromosome 30 of a multi-chromosomal genome, such as the human chromosome, in greatly enlarged form, is shown in FIG. 3. This chromosome is, for present purposes, assumed to have been counterstained by either a probe composition of this invention or by a chemical type stain of the prior art.

When the genomic counterstaining agent is a nucleotide staining chemical-type counterstain of the prior art which has been used as taught in the prior art and which, as a result, intercalates between adjacent nucleotides or binds to an outer surface or groove of the DNA helix, the resulting counterstained DNA as shown in FIG. 3 under even substantially higher magnification is theorized to have an appearance such as illustrated in FIG. 4. Individual nucleotides and base pairs between two strands are represented as small lines connecting the longer lines which represent the backbone of the DNA sequence strand existing in the chromosome. Many fewer nucleotides and base pairs are here shown for schematic purposes than actually exist, and the helical structure is reduced or absent for present illustrative purposes. Thus, molecules of this chemical counterstain are located at each of a plurality of discrete positions 11 along strands 12 of the helices comprising the DNA of chromosome 10. These positions 11 are essentially randomly located along such DNA helix strands 12 and may exist within several base pairs, of one another at high concentrations of the prior art nucleotide counterstain. Even though intensity variations can occur and are observable, because of the close spacing between the chemical counterstain molecules, the chromosome 10 under microscopic examination appears to be substantially completely stained.

When, alternatively, the genomic counterstaining agent is a probe composition of the present invention which has been used in an in situ hybridization procedure under hybridizing conditions such as described herein to form hybrids with genomic DNA, the resulting counterstained DNA as shown in FIG. 3 under such substantially higher magnification is theorized to have an appearance such as illustrated in FIG. 5. Thus, individual ones of the DNA segments 13 present in the probe composition of the invention have hybridized to certain single stranded (denatured) regions 14 believed to exist in target DNA strands or sequences 12 as a result of denaturation (and preferably also dehydration) processing. It is theorized and presumed that not all such denatured regions hybridize with every individual DNA segment that is present in the probe composition, as illustrated by the unhybridized region 14 shown in FIG. 5. Thus, such individual hybridized DNA segments of the probe composition are located at a plurality of discrete locations or positions or regions 14 along strands 12 of the helices comprising the DNA of chromosome 10. These positions 14 are believed to be located along such DNA helix strands 12 with significant areas typically existing between adjacent positions 14 along a single DNA strand 12 and also between adjacent positions 14 existing between adjacent portions of strand 12. Since each of such hybridized DNA segments of the probe composition is here labeled with at least one fluorophore group, the chromosome 10 appears under a fluorescent microscopic examination to be substantially completely stained even though there is, in fact, a spacing between the adjacent labeled probe segments relative to the DNA sequences of chromosome 10 because of the above indicated limited resolving characteristics of the conventional light microscope.

As illustrated in FIG. 6, a resulting genomically counterstained chromosome or group of chromosomes, whether the counterstain is achieved by using a prior art intercalating chemical counterstain or a genomically hybridizing probe composition of the present invention, can have the same or similar appearance, particularly if the respective counterstains each have the same or similar fluorescent color. The advantages of a genomic counterstain achieved with a probe composition of the invention are elsewhere explained herein.

The features and utilities of the invention are further illustrated by reference to the photomicrographs of FIGS. 7 through 15. Each of the photomicrographs of FIGS. 7 through 15 show slide mounted specimens containing metaphase chromosome spreads and interphase nuclei derived from human blood cells. Such specimens have all been subjected to in situ hybridization under hybridizing conditions with genomic counterstain compositions. All the photomicrographs involve the same magnification as shown by the 10 micron spacer line marked on each of these photomicrographs, and all of the photomicrographs were prepared using the same fluorescence microscope with each specimen being illuminated with light from a 100 watt mercury arc lamp. The fluorescent colors involved, of course, do not show in the appended black and white photomicrographs (which were submitted since the U.S. Patent and Trademark Office does not utilize color photomicrographs at this time).

Figure 7:
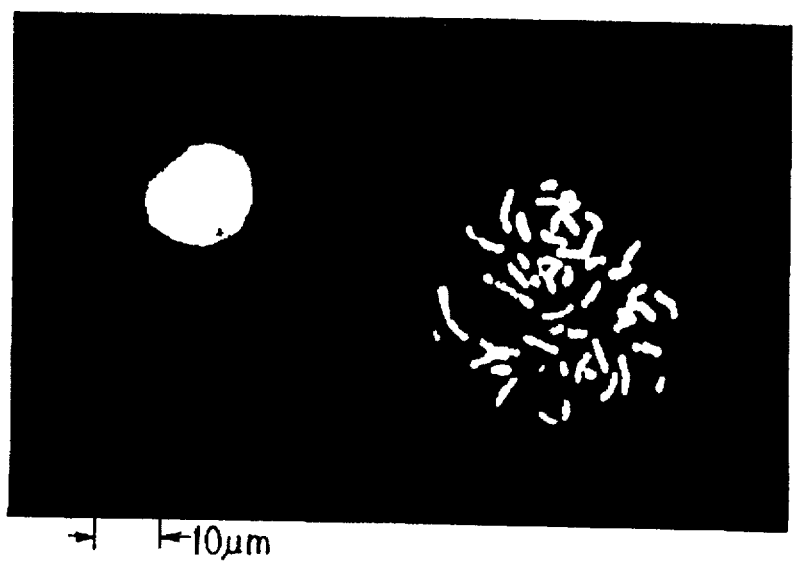

FIG. 7 shows a specimen having a single interphase nucleus (left of center) and a single spread of metaphase chromosomes (right of center). The specimen was counterstained using 600 ng of 0.95% DECCA-labeled fragmented human placental DNA prepared as described in Example 6 below (using preparation #2 listed below in Table IV and employing the 10 µl hybridization solution described in Example 15(a) below). Hybridization was here carried out as described in Example 15(a) below, and the genomically hybridized and counterstained specimen was observed and photographed using a fluorescence microscope equipped with filter #13 identified below in Table IV.

Figure 8:
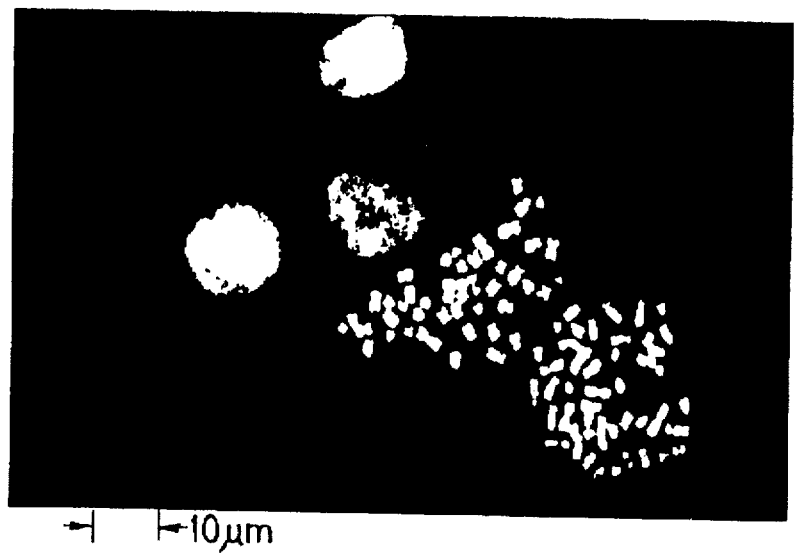

FIG. 8 shows a specimen having three interphase nuclei and two metaphase spreads counterstained in the same manner as in FIG. 7 except that 1 µg of Cot-1 was included in the hybridization solution as a blocking DNA. The intensity of DECCA fluorescence (identically observed and photographed as in FIG. 7) in the hybridized genomically counterstained chromosomes was reduced somewhat, but the staining was still quite distinct and substantially complete.

Figure 9:
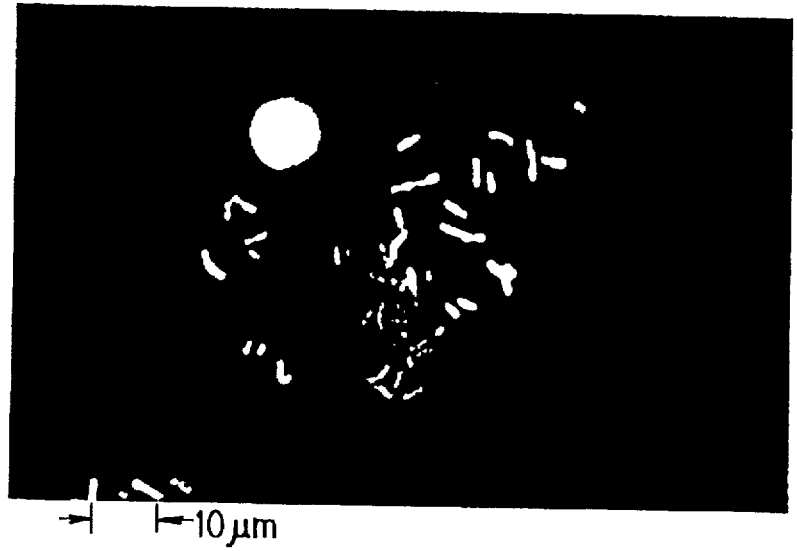

FIG. 9 shows a specimen having an interphase nucleus and a single metaphase spread counterstained in the same manner as FIG. 7 except that 2 µg of human placental DNA was included in the hybridization solution as a blocking DNA (in place of Cot-1 DNA). The intensity of the DECCA fluorescence (identically observed and photographed as in FIG. 7) was reduced somewhat, but the staining was still quite distinct and substantially complete.

The results shown in FIGS. 7 through 9 thus demonstrate and illustrate that the genomic DNA counterstaining probe compositions of this invention can be used either alone or in combination with other blocking DNA from the same genome, sharing the same target regions, while still providing visually detectable complete identification of a genome, here the human genome. These results also show that blocking DNA of the same genome, here illustratively human placental DNA and Cot-1 DNA, can be used with a genomic probe composition of this invention when required or desired by a particular usage.

Figure 10:
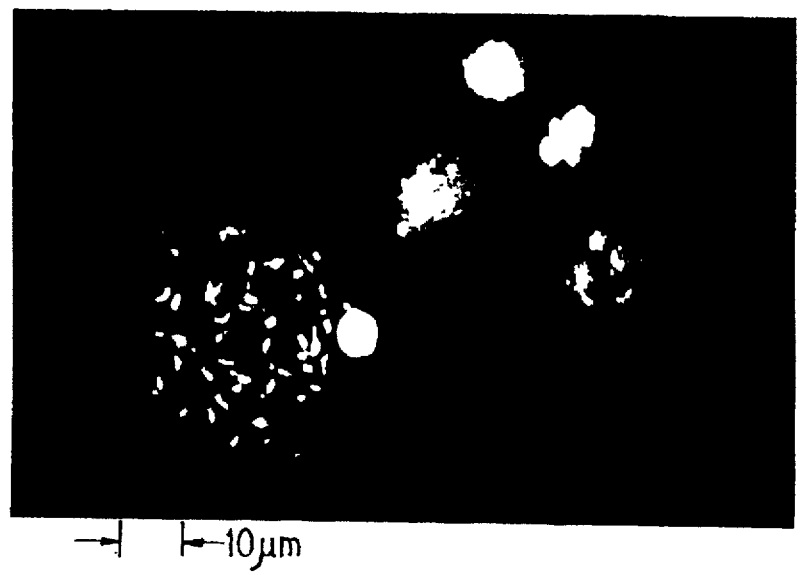

FIG. 10 shows a specimen having several interphase nuclei and a single metaphase spread. The specimen was counterstained with 100 ng of 3.6% CTMR-labeled Cot-1 DNA prepared as described in Example 4 below (using preparation #6 listed in Table II) and using the same 10 µl hybridization solution. Hybridization was carried out as described in Example 15(a) below, and the specimen was photographed using the fluorescence microscope equipped with the filter #16 that is specific for CTMR fluorescence as shown in Table III below.

Figure 11:
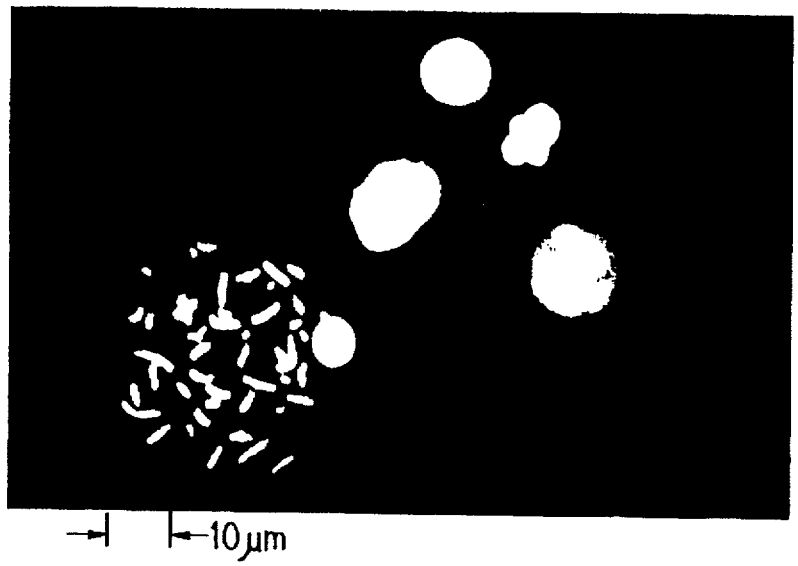

The brightly stained and less brightly stained regions described in Table VI (below) that are characteristic for labeled Cot-1 DNA-based probe compositions of this invention are clearly visible in FIG. 10, yet the specimen material is completely stained FIG. 11 shows the same specimen as in FIG. 10 which was stained with the prior art (convention) chemical counterstain DAPI by adding the DAPI to the antifade solution as described in Example 15(a). The DAPI fluorescence in the resulting specimen was observed and photographed using the fluorescence microscope equipped with filter #1 that is specific for DAPI excitation and emission (see Table IV below).

Comparison of FIG. 11 to FIG. 10 demonstrates that the Cot-1 based probe composition in FIG. 10 completely highlights all chromosomal material in the specimen similarly to DAPI.

Figure 12:
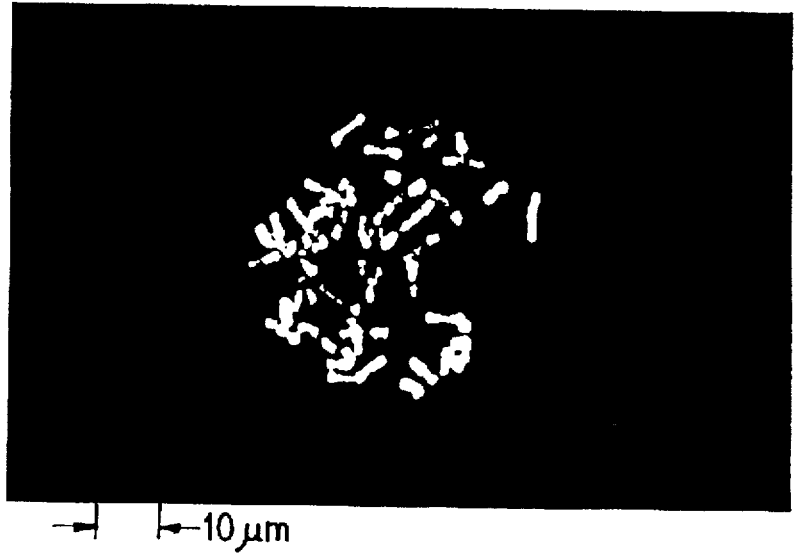
Figure 13:
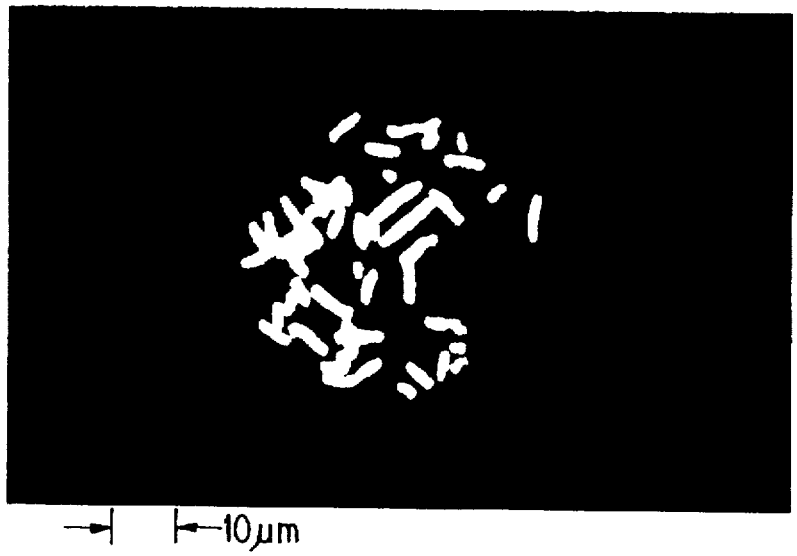

A similar comparison is accomplished with the photomicrographs of FIGS. 12 and 13 which involve the same specimen. The specimen shows a single metaphase spread of chromosomes. FIG. 12 resulted from subjecting this specimen to an in situ hybridization procedure carried out as above described for the specimen of FIG. 10 except that the hybridization solution contained 100 ng of 1.8% CTMR labeled cosmid library fragmented DNA which was prepared as described in Example 4.3 below (using preparation #9 listed in Table IV below). The resulting hybridized specimen was observed and photomicrographed by the same procedure used in FIG. 10 above.

In FIG. 13, the specimen was stained with DAPI by the same procedure above described for FIG. 11 and then was observed and photographed as above described for FIG. 11.

Comparison of FIG. 12 to FIG. 13 shows that, while variations in CTMR fluorescence intensity are observed along the length of each counterstained chromosome, the counterstaining achieved by the CTMR probe composition here is still complete for each chromosome when compared to the fluorescence achieved with the prior art DAPI counterstain.

Figure 14:
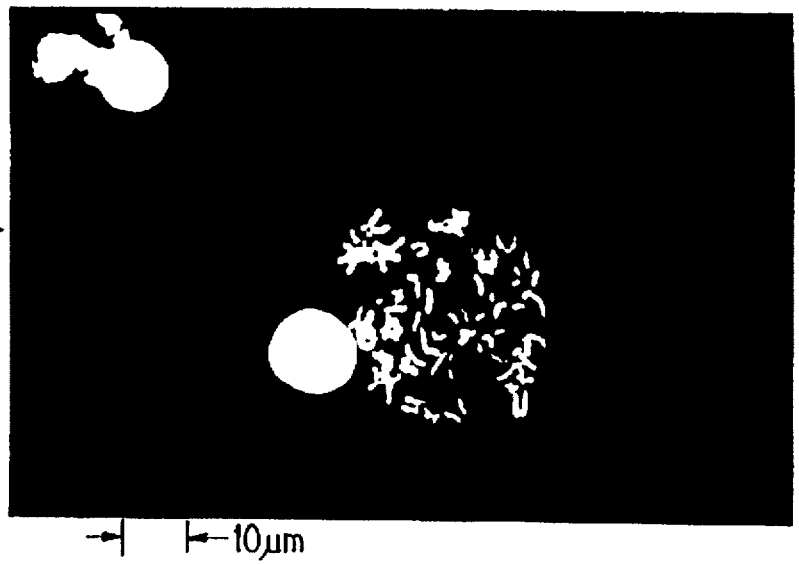
Figure 15:
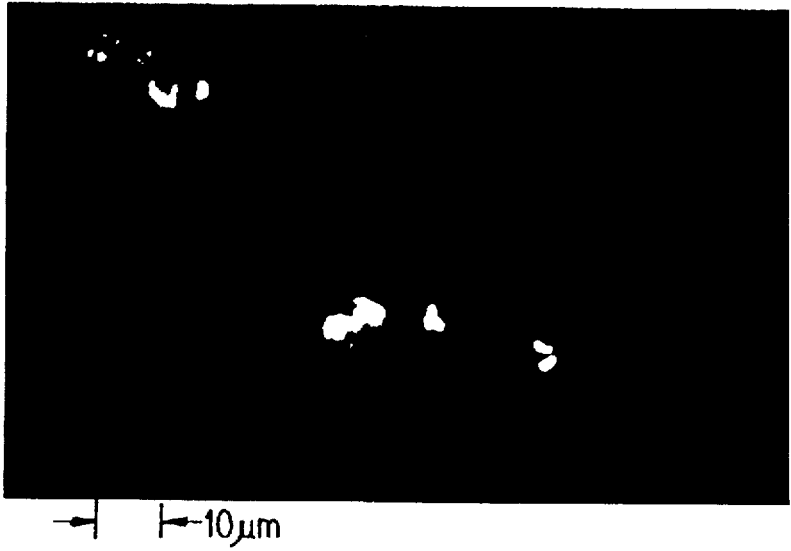

FIGS. 14 and 15 show photomicrographs of the same specimen which contains two interphase nuclei and one metaphase spread. In situ hybridization was carried out by the procedure described in Example 15(a) below using in admixture (a) 600 ng of 0.95% DECCA-labeled fragmented human placental DNA (prepared as described in Example 6 below using preparation #2 of Table IV below), (b) 100 ng of 2.0% CTMR labeled whole chromosome #8 specific probe composition (prepared as described in Example 10 below), and (c) 1 µg of Cot-1 as a blocking DNA all in the 10 µl hybridization solution. The photomicrograph of FIG. 14 was taken with the microscope fitted with the DECCA specific filter #13 (see Table III), while the photomicrograph of FIG. 15 was taken with the microscope fitted with the CTMR specific filter #16 (see Table III).

The photomicrograph of FIG. 14 shows complete staining of the chromosomes in the metaphase spread and also of the interphase nuclei. The photomicrograph of FIG. 15 shows clearly and distinctly both (a) one pair of chromosomes in the metaphase spread brightly stained, and also (b) two brightly stained regions in each of the interphase nuclei corresponding to the same but distended chromosome pair. Thus, FIGS. 14 and 15 demonstrate and illustrate that chromosome specific probe compositions which contain DNA segments, like the genomic counterstaining probe compositions of this invention, are directly labeled with fluorophores, can be admixed with the genomic probe compositions of this invention. Also, such FIGS. 14 and 15 demonstrate that such mixtures can be used in hybridization procedures without altering the subsequent capacity to distinguish both the specifically stained chromosomal DNA regions and the totally genomically stained DNA in the same specimen.

(D) In situ Hybridization and Genomic Counterstaining

Probe compositions of this invention are well suited for use in hybridization procedures as genomic counterstains.

The invention thus provides a process for identifying genomic DNA present in a specimen that is derived from an organism which has a multichromosomal genome. The process involves the sequential steps of (a) contacting the specimen under hybridizing conditions with a probe composition of the invention to produce hybrids between the target genomic DNA present in the specimen and the probe DNA segments present in the probe composition, (b) separating from the resulting specimen residual portions of the probe composition, and (c) examining the resulting specimen.

The specimen examining can be variously accomplished, for example, with a fluorescent microscope, a flow cytometer, or the like. Examination involves irradiating the resulting specimen with energy which is at least sufficient to cause fluorophore groups present in the hybrids to fluoresce while concurrently detecting the resulting fluorescent energy so produced. As those skilled in the art will appreciate, depending upon the particular objectives and conditions utilized, this process of examining or identifying can be practiced without the separating step if the level of residual probe composition is so low as not to interfere with the examination.

Advantageously, any convenient or particular in situ hybridization procedure can be used in the practice of this aspect of the present invention. An in situ hybridization procedure can involve a particular specimen which contains all or only a fraction of the total genomic DNA of the originating organism.

Currently, a present preference is to use a probe composition of this invention in in situ hybridization procedures of the type that are commonly and conveniently carried out on specimens which have preliminarily been prepared and mounted on a slide, such as a slide comprised of glass or the like. For purposes of practicing such an in situ hybridization procedure of the present invention, conventional slide preparation procedures can be employed, such as taught, for example by F. T. Bosman, M. Van der Ploeg, A. Schaberg, and P. Van Duijn (1975) *Genetica*, Vol. 5, p. 425–433, Galland Pardue (1969) *Proc. Natl. Acad. Sci. USA* Vol. 64, p. 600, and conventional in situ hybridization procedures can be employed, such as taught, for example, by B. Bhatt, J. Burns, D. Flannery and J. O'D. McGee (1988) *Nucleic Acids Research*, Vol. 16 pp. 3951–3961, and A. H. N. Hopman, J. Wiegart and P. Van Duijn (1987) *Experimental Cell Research*, Vol. 169, pp. 357–368.

To accomplish total genomic DNA counterstaining and detection of such a slide mounted and processed specimen using a probe composition of this invention, the following illustrative procedure can be carried out:

Preferably, such slide mounted specimen is preliminarily processed to dehydrate at least partially and also denature at least partially the DNA that is presumed to be present therein. Conventional denaturing and dehydrating procedures can be employed. Illustrative denaturing solutions and use procedures are exemplified in the Embodiments below provided, as are illustrative hybridization solution and use procedures. Preferably such procedures do not result in appreciable alteration or loss in the DNA identity or structure of any chromosomes present in the specimen. Thereafter, the following sequential hybridization step sequence is carried out on the resulting so processed specimen.

First, the slide mounted specimen is contacted with a probe composition of this invention. To conserve such composition, the amount thus used in contacting preferably is the minimum amount required to achieve complete coverage of such specimen surface by such probe composition. There is no inherent functional or process limit, however, upon the maximum or minimum amount of a given probe composition that can be employed for a given slide mounted specimen.

The volume or quantity of such a minimum probe amount is influenced by the particular procedure and equipment being utilized. For example, in a situation where the surface area of the specimen is in the range of about 500 mm$^2$, and the specimen is uniformly deposited upon an inert slide surface, such as the surface of a conventional glass slide, in a coating thickness of about 1 micron, about 10 µl of a drop of a probe composition (as above described) can be deposited upon and spread over such specimen surface. The amount used should be sufficient to achieve a complete wetting and contacting of such surface by such probe composition. Thereafter, a conventional cover slip or the like can be overlaid upon such surface, and compressed against such.

It will be appreciated that any convenient contacting procedure and associated equipment can be employed. At the time of the contacting, the probe composition and the specimen are preferably already at a uniform temperature that is in the range of about 30° to about 45° C. although higher and lower temperatures can be employed, if desired depending upon the salt and denaturant concentration in the hybridization solution. The specimen is always preferably uniformly contacted with the treating probe composition.

Next, the combination of the specimen and the treating probe composition that is in contact therewith are subjected to an incubation period which is typically and preferably in the range of about 60 to about 1,000 minutes, though longer and shorter incubation period times can be employed, if desired. During the incubation period, the temperature is preferably maintained in the above indicated range of about 30° to about 45° C.

During this incubation period, the treating probe composition undergoes hybridization with the genomic DNA that is present in the specimen. The probe composition penetrates into and through such specimen and is capable of hybridizing with the genomic DNA so present to form hybrids. Owing to the nature and the composition of the total genomic DNA that is incorporated into the treating probe composition, the treating probe composition characteristically is observed to hybridize with genomic DNA present in the specimen in a continuous and preferably complete manner consistent with observations herein presented.

Next, at the end of the incubation time period, the resulting specimen is subjected to a liquid washing procedure that is adapted to separate therefrom unreacted, residual treating probe composition. Advantageously, washing procedures similar to those known to the prior art of in situ hybridization can be used (for example see Bhatt et al (1988) *Nucleic Acids Research* 16, 3951–3961). Usually several different wash baths are employed which contain NaCl, buffer salts, such as sodium citrate and the like, and formamide, at various concentrations. Higher formamide concentrations and lower NaCl concentrations are used for higher stringency (greater ability to remove residual probe DNA). Also detergents can be used, especially in the last bath. Stringency is also increased by raising the temperature of the wash baths above room temperature. While high stringency favors removal of unhybridized probe, it also favors removal of a small amount of the hybridized probes, for example, the shorter probe segments or probes hybridized to only partially accessible regions of the chromosomes such that not all the individual probe nucleotides form base pairs with the adjacent chromosome nucleotides. This in effect reduces ultimate signal intensity, therefore placing limits on the allowed stringency.

For example, one effective procedure uses sequentially three baths at 45° C., each contain 50% formamide and 2×SSC (read as twice the concentration of standard SCC buffer, where standard SSC buffer contains 0.15M NaCl and 15 mM sodium citrate at pH7, a fourth bath at 45° C. containing 2×SSC, and a fifth bath at 45° C. containing 2×SSC and 0.1% NP-40 (a nonionic detergent which can be obtained from Calbiochem, La Jolla, Calif.). The time permitted for soaking a slide in each bath can be varied from seconds to minutes to achieve varying degrees of unhybridized probe removal, with incubations longer than 10 minutes per bath not improving removal of unhybridized probe. The number of baths can also be reduced while achieving reasonable unhybridized probe removal for most specimens, while increasing the number of baths provides an improvement which can be considered to be negligible. After soaking in the last bath, the slide is allowed to drain preferably in a near vertical position and to be fully or partially air-dried prior to subsequent adding of a mounting medium and covering with a coverslip. The mounting medium usually and conventionally contains glycerol, buffer salts, and an antifade material which reduces the rate of photo-oxidation of the fluorophore labels, as those skilled in the art will appreciate.

The slides can be viewed after processing immediately under a fluorescence microscope, or they can be stored at room temperature for several days or the like before examination. Storage at −20° C. preferably in an inert gas (e.g., nitrogen or argon) environment, is presently preferred for extended storage periods to guard against changes in hybridized targets, specimen deterioration, or the like.

The resulting slide mounted specimen can be further hybridized with other probe preparations. For example, the coverslip can be removed, and the slide can be soaked (immersed) in one of the wash baths to remove the mounting solution. A preferably denatured second probe hybridization solution is then applied (as above described) to the slide (the slide is not denatured a second time), the resulting slide incubated to allow hybridization, and then the slide is washed, as described above for the first hybridization procedure.

Thereafter, a resulting so processed and counterstained product slide mounted specimen can be subjected to microscopic examination using a conventional fluorescence microscope and conventional filters. In the case of examining a genomically counterstained specimen produced from a probe composition of this invention, as those skilled in the art will appreciate, the particular filter used is preferably one which is matched to the spectral response characteristics associated with the particular fluorophore that is involved as the label moiety in a given probe composition of this invention. Such a filter is either commercially available or readily made by conventional filter-making or filter assembly technology. The following Table IV presents illustrative specifications for filters and such filters were used with the fluorophores included in the Examples herein presented.

TABLE IV

FLUORESCENCE MICROSCOPE FILTER SET NOMINAL SPECIFICATIONS

| Fluorophore | Excitation Filter[†] | Dichroic Beamsplitter[††] | Emission Filter[†] | Filter Set Ref. # |
|---|---|---|---|---|
| AMCA/DAPI | BP 365 (>50)* | 395 | LP 420 | 1 |
|  | BP 360 (50)** | 400 | BP 450 (50) | 2 |
| CBAA | BP 360 (50)** | 400 | BP 425 (35) | 11 |
| HCCA | BP 400 (20)** | 440 | BP 456 (28) | 12 |
| DECCA | BP 435 (20)** | 475 | BP 535 (45) | 3 |
|  | BP 432 (20)** | 455 | BP 478 (32) | 13 |
| FITC | BP 470 (40)* | 510 | LP 520 | 4 |
|  | BP 485 (20)* | 510 | BP 540 (50) | 5 |
|  | BP 480 (30)** | 505 | BP 535 (45) | 6 |
|  | BP 496 (24)** | 515 | BP 532 (28) | 14 |
| CFI | (same as for FITC) | | | |
| DMPB | (same as for FITC) | | | |
| FCHA | (same as for FITC) | | | |
| FAP | (same as for FITC) | | | |
| ETC | BP 518 (26)** | 545 | BP 558 (30) | 15 |
| ErITC | (same filters as EITC, although not optimal for this fluorophore - should be shifted to longer excitation and emission wavelengths relative to EITC) | | | |
| TRITC | BP 546 (12)* | 580 | LP 590 | 7 |
|  | BP 540 (23)** | 570 | BP 605 (55) | 8 |
|  | BP 552 (23)** | 567 | BP 590 9(25) | 16 |
| CTMR | (same as for TRITC) | | | |
| LisR | (same as for TRITC or Tx Rd) | | | |

TABLE IV-continued

FLUORESCENCE MICROSCOPE FILTER SET NOMINAL SPECIFICATIONS

| Fluorophore | Excitation Filter† | Dichroic Beamsplitter†† | Emission Filter† | Filter Set Ref. # |
|---|---|---|---|---|
| Tx Rd | BP 560 (40)** | 595 | BP 635 (60) | 9 |
| CXR | | (same as for Tx Rd) | | |
| Propidium iodide | BP 540 (23)** | 565 | BP 615 (30) | 10 |

†Wavelength values are listed in units of nanometers. Bandpass filters are marked "BP" with the center of the filter's transmission band listed first and the full width at half maximum enclosed in parenthesis. Long pass filters are marked "LP" with the transition region between low and high tramsission indicated.
††Wavelength values are listed in units of nanometers and indicate the region of the filter's transition between high reflectance and high transmission.
*Filter set obtained from Zeiss.
**Filter set obtained from Omega Optical.

The completeness, the intensity, and the distribution of the coloration associated with the counterstaining thus achieved can be used, if desired, as an indication of the suitability of the product processed specimen for further in situ hybridization processing. For example, the counterstaining can be used as an indication of whether or not the product specimen is suitable for a further sequential in situ hybridization procedure wherein another, or other, probes, or probe compositions, are applied thereto which are hybridizable to specific targets present in predetermined chromosomes, or chromosome regions, or the like. Alternatively, a genome counterstain probe of this invention can be admixed with a more specific probe preparation so that upon subsequent examination, hybridizable regions of the specimen can be distinguished from substantially non-hybridizable regions of the specimen.

Those skilled in the art will appreciate that in in situ hybridization of a slide mounted specimen, the sequence of (a) contacting and (b) separating (as above indicated) can be advantageously carried out more than once before the step (c) (examining) as above indicated is carried out. In each such repeat of steps (a) and (b) (each of which is conveniently carried out as above described herein), a different probe composition is employed, with a probe composition of this invention being employed on one repeat, and with another (different) probe composition being employed in each of the other such repeats, each such other probe composition being targeted to a different predetermined fractional region of said genome.

The genomic counterstaining probe compositions of this invention can also be used, for another example of utilization, in a procedure utilizing fluorescence activated flow cytometry. For instance, initially chromosomes can be conventionally isolated, for instance, from mitotic cells of a cell culture; but see, for example, Carrano et al. "Measurement and Purification of Human Chromosomes by Flow Cytometry and Sorting" Proc. Nat'l. Acad. Sci. U.S.A., Vol. 76, pp. 1382–1384 (1979).

Next, an aqueous dispersion of the so isolated chromosomes has admixed therewith a crosslinking agent for the protein (i.e., histones and nonhistones) present in the chromosomal chromatin with the DNA. Conveniently, the crosslinking agent reacts with a polar group of one or more polar group containing amino acids present in such protein, such as, for example, asparate, aspargine, arginine, glutamate, glutamine, histidine, lysine, serine, tyrosine, and tryptophan. The sulfhydro group of cysteine can also sometimes crosslink. A suitable crosslinking agent and a suitable in situ hybridization procedure are taught, for example, in Van den Engh, U.S. Pat. No. 4,770,992 (1988).

A probe composition of the invention is admixed with the crosslinked and preferably denatured chromosomes.

A resulting mixture is preferably subjected to a separation procedure to isolate unhybridized residual probe composition. However, as those skilled in the art will appreciate, if the concentration of residual probe composition is sufficiently low so as not to interfere, or excessively interfere, with the particular flow cytometric analysis contemplated, then such separation procedure can be circumvented.

A resulting suspension is subjected to flow cytometric analysis using, for example, a dual beam cytometer such as described, for example, in the above cited references.

The results so measured can be used, for example, to identify chromosomes based upon the gross specimen morphology, or to correlate the presence of a specific chromosome stain with the presence of any chromosome material. The correlation is made to discriminate against the background which could be confused with the specific stain.

Another technique combining flow cytometric detection with in situ hybridization using a probe composition of this invention uses interphase nuclei in suspension in the manner taught, for example, by Trask et al. in Hum. Genet., 78:251–259 (1988).

It is an important feature and advantage of the probe compositions of this invention that they can be admixed with other probe compositions without adversely affecting the chemical structure or the functional capacity thereof. For example, prior to the first procedural step above indicated, a probe composition of this invention, prepared as above described, can be admixed, if desired, with another probe composition which, for example, contains probes that are hybridizable to specific targets present in predetermined chromosomes, or chromosome regions. Such other probe compositions should preferably be suitable for usage in in situ hybridization under comparable conditions of temperature, time, and the like (relative to a probe composition of this invention).

For example, such other probe composition can be a direct labeled or an indirect labeled probe composition such as (a) a direct labeled paint probe composition or a direct-label centromere specific probe composition such as are taught in the Bittner et al. copending U.S. patent application Ser. No. 07/762,913, now U.S. Pat. No. 5,491,224 filed on even date herewith and identified by the assignee Docket No. 31,433, such teachings being incorporated herein by reference; (b) a probe composition labeled by nick translation of the probe DNA with fluorophore-labeled nucleoside triphosphates as described in Wiegant et al. (1991) Nucleic Acids Research 19, 3237–3241; (c) the indirect labeled probe composition prepared by incorporating biotin- or digoxygenin-containing deoxynucleotide triphosphates into probe DNA as described in a number of publications including Wiegant et al. (op. cited) and Bhatt et al. (1988) *Nucleic Acids Research* 16, 3951–3961; (d) the indirect labeled probe compositions which contain chemical groups that react in a post hybridization reaction with chemical groups on modified fluorophores to form a bond between hybridized probe and fluorophore label, as described by Hopman et al. (1987) *Experimental Cell Research* 169, 357–368; and the like.

Such a resulting mixed probe composition is then used in an in situ hybridization procedure in a slide mounted specimen. In this procedure, the genomic DNA target bodie(s) present in the specimen is/are counterstained with at least one DNA probe composition of this invention and the specific target(s), to the extent, if any, that such is/are present in the specimen, is/are also concurrently stained with the single and/or admixed probe composition(s). Residual probes are subsequently separated from the resulting specimen in the same washing step procedure.

Another feature and advantage of the probe compositions of this invention is that they can also be used for counterstaining even after the completion of a preceding specific hybridization procedure, such as an in situ hybridization procedure wherein a particular chromosome or particular region of a particular chromosome was the target of a particular probe composition, or the like.

The presently preferred probe compositions of this invention are characterized by a capacity to completely and substantially evenly counterstain genomic DNA, thus effectively outlining the individual chromosomes or chromosome fragments present in a specimen so that such bodies are detectable under a fluorescence microscope or the like.

A counterstain produced by hybridization of a target with a probe composition of this invention can be distinguished from a prior art chemical counterstain by, for example, dilution of the resulting stained specimen. A chemical counterstain characteristically dissociates from the chromosomal DNA much more readily than does a hybridized probe. This is because the equilibrium binding constant for two complementary DNA strands in the size range of about 150 to about 600 base pairs, as used in this application, is extremely large when the temperature is several degrees or more below the melting temperature of the complementary strands ($T_m$). For example, a complementary 20-nucleotide long pair of oligomers has an association constant of about $2 \times 10^{24} M^{-1}$ at 25° C. (calculated from its standard free energy). Chemical counterstains have association constants usually well below $10^{10} M^{-1}$. Dilution of the counterstain can take the form of washing steps, exactly as are performed as described above for washing the slide-mounted specimens to remove unhybridized DNA. In fact, soaking a specimen stained with either DAPI or propidium iodide, two of the most common chemical counterstains for chromosomes, sequentially in three baths at 45° C., each containing 50% formamide and 2×SSC, a fourth bath at 45° C. containing 2×SCC, and a fifth bath at 45° C. containing 2×SCC and 0.1% NP-40, serves to greatly reduce the intensity of the chemical counterstain, as determined by visual examination under the fluorescence microscope, to a point that individual interphase nuclei and metaphase spreads are no longer discernible or are just barely visible. This same wash procedure removes substantially only the unhybridized probe and, therefore, not the target hybridized counterstain when the counterstain is a direct-labeled total genomic DNA segment composition such as provided herein.

Probe compositions of this invention are generally compatible with other in situ hybridization reagents. However, in the case of two or more indirect labeled probes in combination, care must be taken that no components are present which will cross-react with each other when in admixture.

Probe compositions of this invention characteristically result in counterstained DNA in a treated specimen, such as a slide mounted specimen, which has a stable fluorescent coloration. Thus, for example, such a specimen can be further processed under further in situ hybridization conditions without substantial removal or diminution of the counterstain intensity caused by dissolution of counterstain into process liquids, as long as hybridizing conditions are maintained.

Embodiments

The present invention is further illustrated by reference to the following Examples.

Fluorescence microscopy was performed using one or more of the following fluorescence microscopes; Zeiss Axioskop, Axioplan or Axiophot. Filters used are shown in Table IV above.

EXAMPLE 1

Preparation of Aminated Human Total Genomic DNA

Aminated DNA was prepared from 3 sources of total human genomic DNA. Human placental DNA (extracted from human tissue) was obtained from Sigma Chemical Co. (St. Louis, Mo., type XIII). Cot-1 DNA was obtained from Life Technologies, Inc. (Gaithersburg, Md., cat #5279SA). The cosmid library (pWE15) of human placental DNA was obtained from Stratagene (La Jolla, Calif.). The library was cultured and DNA was extracted from the library as described in Example 10 Bittner it al. U.S. patent Ser. No. 07/762,912, now U.S. Pat. No. 5,506,350 filed on even date herewith and identified by assignee's Docket No. 30,456. Each DNA was dissolved in 2 ml water and sonicated using a Branson Sonifier model 450 equipped with a microtip probe. The sonication was conducted using 2 2½ minute periods separated from each other by an off period of about 1 minute using a power setting of 3. The duty cycle was 80% on which was approximately 25–30 watts, and 20% off. The sonicated DNA was extracted with an equal volume of 1:1 phenol:chloroform. The DNA was precipitated with ethanol by adding a solution of 2.6M sodium acetate at pH 5.4 in an amount equal to ¹⁄₁₀th the volume of the DNA solution (0.2 ml in this instance) and ethanol in an amount equal to 2–2.5 times the volume of the combined DNA and sodium acetate solution (4.4 to 5.5 ml in this instance) and placing the resulting mixture in a −20° C. freezer overnight. The mixture was then centrifuged at 8,000×g for 10–15 minutes. The supernate was removed and the DNA pellet dried in a centrifugal evaporator (Savant Instruments, Farmingdale, N.Y.).

The amination reaction was conducted by dissolving the purified sonicated DNA in water to achieve a concentration of 4 mg DNA per ml water, and diluting the DNA solution 10-fold with 9 volumes of the ethylenediamine/bisulfite solution. The ethylenediamine/bisulfite solution was prepared just before reaction by adding, in order, 4 ml of water, 7 ml of concentrated HCl, 4 ml of ethylenediamine, 1.9 g of $NaHSO_3$, concentrated HCl to pH 7.0, and water to a final volume of 20 ml. The reaction was allowed to proceed at either 25.0° or 37.0° C. for between 6 hours and 2 days to obtain the desired amount of amination. Following the incubation period, the reaction solution was dialyzed sequentially in three 1–2 liter volumes of 5 mM sodium borate at pH 8.0 and the dialyzed product precipitated with ethanol. This procedure was repeated using different reaction conditions. The results are summarized in Table V below.

EXAMPLE 2

Analysis of Aminated Total Human Genomic DNA

The extent of transamination of deoxycytidine (dC) was determined by enzymatic digestion of the aminated DNA with the enzymes deoxyribonuclease I (DNase I), phosphodiesterase I (PDI), and alkaline phosphatase (Alk. Phos.) followed by separation of the resulting nucleosides on an FPLC chromatography system (Pharmacia LKB, Piscataway, N.J.). 5–10 μg of aminated DNA was diluted with water to 50 μl and the DNA purified on a spin column containing Sephadex G-25 (5Prime 3Prime, Inc., Paoli, Pa.). The DNA was then dried and 12.5 μl of 2×DNase I buffer (20 mM TRIS, 10 mM $MgCl_2$,pH 7.5), 12.0 μl water, and 0.5 μl of DNase I (BRL, 2 mg/474 μl, >10,000 units/mg) added to the DNA and the solution incubated in a 37° C. water bath for 1 hour. 50 μl of 2×PDI/Alk. Phos. buffer (100 mM TRIS, 200 mM NaCl, 28 mM $MgCl_2$, 2 mM $ZnCl_2$, pH 9.0), 1.0–5.0 units of PDI (Pharmacia LKB, 1,000 units dissolved in 1 ml of 1×PDI/Alk. Phos. buffer), 5–10 units of calf intestinal Alk. Phos. (Promega, 1,000–10,000 units/ml), and water to a final reaction volume of 100 μl were then added and the solution incubated for an additional 1–2 hours at 37° C. The digested sample was applied to either a MinoRPC or Pep S column (Pharmacia, LKB) and a linear gradient between buffer A (97.5:2.5 ion-pairing buffer:methanol, ion-pairing buffer=50 mM $KH_2PO_4$, 0.02 to 0.05% hexane-sulfonic acid, pH 7.0) and buffer B (50:50 ion-pairing buffer:methanol) used to elute the sample (a 0.8% increase in buffer B/min at a flow rate of 0.37 ml/min until 40% buffer B was reached, followed by a 3% increase in buffer B/min to 100% buffer B at a flow rate of 0.3 ml/min) while recording the DNA elution profile by absorbance. Each of the 4 natural deoxynucleosides and the transamination product of deoxycytidine were eluted separately and the amount of deoxycytidine transaminated was determined from the relative areas under the deoxycytidine and transaminated deoxycytidine peaks in the elution profile. The results are listed in Table V below for nine preparations of aminated total human genomic DNA.

TABLE V

Transamination Reaction Conditions and Percent Modification of dC

| Aminated DNA Preparation Identification No. | Human Genomic DNA | Temp (°C.) | Reaction Time | % dC Aminated[a] |
|---|---|---|---|---|
| 1 | placental tissue | 37 | 2 day | 67 |
| 2 | placental tissue | 25 | 15 hr | 12 |
| 3 | placental tissue | 25 | 15 hr | 9.5 |
| 4 | placental tissue | 25 | 6 hr | 3.8 |
| 5 | $C_ot$-1 | 37 | 2 day | 41 |
| 6 | $C_ot$-1 | 25 | 15 hr | 10 |
| 7 | $C_ot$-1 | 25 | 6 hr | N.D.[b] |
| 8 | cosmid library | 25 | 15 hr | 10 |
| 9 | cosmid library | 25 | 6 hr | 3.1 |

[a]The percentage of total nucleotides aminated is 0.25 times the % dC aminated, assuming that each of the 4 different nucleotides is present in equal amount.
[b]N.D. signifies that the % amination was not determined due to an impurity which co-eluted with the aminated dC on the Pep S column. The % amination should be between 3 and 4 by comparison to the human placental DN and the cosmid library DNA aminated using the same reaction conditions.

EXAMPLE 3

Preparation of FITC-Labeled Human Placental DNA

40 μg each of aminated DNA preparation no. 3 and no. 4 were separately dissolved in 235 μl of buffer consisting of 0.05M sodium borate at pH 9.3. To each of these were added 15.2 μl of 20 mM FITC in dimethylsulfoxide and the resulting solutions were continually inverted overnight (approximately 18 hr) in the dark at room temperature. Following reaction, the reaction products were precipitated with ethanol, in the same manner as described in Example 1. The dried products were each dissolved in 300 μl of water and the solutions applied to 1 cm I.D.×30 cm high Econo-Columns filled with Sephadex G-25 and eluted with water. The labeled materials eluting at the column void volumes were collected and again precipitated with ethanol to provide the purified labeled DNA. Stock solutions of the purified labeled DNA were prepared by dissolving the dried products in a small volume of water.

The DNA concentration and degree of labeling were determined as follows: 10 μl of a labeled DNA stock solution was diluted to 1 ml with 10 mM tris (hydroxymethyl) aminomethane at pH 8.0 and the absorbance spectrum of this solution measured to provide the absorbance at 260 nm, $A_{260}$, and the absorbance at the long wavelength absorbance maximum of the label, $A_{max,label}$. The concentration of label was calculated by dividing $A_{max,label}$ by the extinction coefficient of the label at the long wavelength absorbance maximum listed in the Molecular Probes Handbook of Fluorescent Probes and Research Chemicals (Richard Haugland author, Molecular Probes, Inc., 1989). The nucleotide concentration was calculated by dividing $A_{260}$ by the average nucleotide extinction coefficient of $10,000 M^{-1} cm^{-1}$ at 260 nm, after the contribution to the absorbance at 260 nm due to the label alone, $A_{260,label}$, was subtracted from $A_{260}$. $A_{260,label}$ was estimated by determining $A_{260,label}/A_{max,label}$ for a solution of pure unconjugated label and multiplying this value by $A_{max,label}$ measured for the labeled nucleotides solution. The fraction of nucleotides labeled is calculated by dividing the label concentration by the nucleotide concentration. The DNA concentration in μg/ml is calculated from the molar concentration of the nucleotides using an average nucleotide molecular weight of 350 daltons.

EXAMPLE 4

Preparation of CTMR-Labeled Human Placental DNA 4.1 40 μg each of aminated human placental DNA preparation #2 and aminated Cot-1 DNA preparation #6 were separately dissolved in 370 μl of buffer consisting of 0.2M 3-[N-morpholino]propanesulfonic acid at pH 7.4. To each of these was added 30.3 μl of 30 mM CTMR in dimethylformamide and the solutions continually inverted overnight (approximately 18 hr) in the dark at room temperature. Following reaction, the DNA was precipitated with ethanol, in the same manner as described in Example 1. The dried products were each dissolved in 300 μl of water and the solutions applied to 1 cm I.D.×30 cm high Econo-Columns filled with Sephadex G-25 and eluted with water. The labeled materials eluting at the column void volumes were collected and again precipitated with ethanol to provide the purified labeled DNA. Stock solutions of the purified labeled DNA were prepared by dissolving each of the dried products in a small volume of water. The DNA concentration and degree of labeling were determined as described in Example 3.

4.2 In another procedure, 100 μg aminated human placental DNA preparation #4 was labeled with CTMR by dissolving the DNA in 888 μl of 0.2M 3-[N-morpholino] propanesulfonic acid at pH 7.4 and adding 114 μl of 20 mM CTMR in dimethylformamide. Reactions and purifications were conducted as described for the other CTMR reactions.

4.3 In further procedures, 50 μg of aminated Cot-1 DNA preparation #5, #6, and #7, aminated human placental DNA preparation #1, and aminated cosmid library DNA preparations #8 and #9 were labeled with CTMR by separately dissolving each in 444 μl of 0.2M 3-[N-morpholino] propanesulfonic acid at pH 7.4 and adding 57 μl of 20 mM CTMR in dimethylformamide. Reactions and purifications were conducted as described for the other CTMR reactions. 100 μg of aminated human placental DNA preparation #4 was similarly labeled by reaction in 888 μl 0.2M 3-[N-morpholino]propanesulfonic acid at pH 7.4 and 111 μof 20 mM CTMR in dimethylformamide.

EXAMPLE 5

Preparation of Tx Rd-Labeled Human Placental DNA

100 μg of aminated human placental DNA preparation #4 was dissolved in 888 μl buffer consisting of 50 mM sodium borate at pH 9.3. To this was added 114 μl of 20 mM Tx Rd in dimethylformamide and the solution continually inverted overnight (approximately 18 hr) in the dark at room temperature. Following reaction, the DNA was precipitated with ethanol, in the same manner as described in Example 1. The dried DNA was dissolved in 300 μl of water and the solution applied to a 1 cm I.D.×30 cm high Econo-Column filled with Sephadex G-25 and eluted with water. The labeled material eluting at the void volume was collected and again precipitated with ethanol to provide the purified labeled DNA. A stock solution of the purified labeled DNA was prepared by dissolving the dried product in a small volume of water. The DNA concentration and degree of labeling were determined as described in Example 3.

EXAMPLE 6

Preparation of DECCA-Labeled Human Placental DNA

50 μg of aminated human placental DNA preparation #2 was dissolved in 444 μl of buffer consisting of 0.2M 3-[N-morpholino]propanesulfonic acid at pH 7.4. To this was added 57 μl of 20 mM DECCA in dimethylformamide and the solution continually inverted overnight (approximately 18 hr) in the dark at room temperature. Following reaction, the DNA was precipitated with ethanol, in the same manner as described in Example 1. The dried product was dissolved in 300 μl of water and the solution applied to a 1 cm I.D.×30 cm high Econo-Column filled with Sephadex G-25 and eluted with water. The labeled material eluting at the column void volume was collected and again precipitated with ethanol to provide the purified labeled DNA. A stock solution of the purified labeled DNA was prepared by dissolving the dried products in a small volume of water. The DNA concentration and degree of labeling were determined as described in Example 3.

EXAMPLE 7

Preparation of AMCA-Labeled Human Placental DNA

50 μg of aminated human placental DNA preparation #2 was dissolved in 444 μl of buffer consisting of 0.2M 3-[N-morpholino]propanesulfonic acid at pH 7.4. To this was added 57 μl of 20 mM AMCA in dimethylsulfoxide and the solution continually inverted overnight (approximately 18 hr) in the dark at room temperature. Following reaction, the DNA was precipitated with ethanol, in the same manner as described in Example 1. The dried product was dissolved in 300 μl of water and the solution applied to a 1 cm I.D.×30 cm high Econo-Column filled with Sephadex G-25 and eluted with water. The labeled material eluting at the column void volume was collected and again precipitated with ethanol to provide the purified labeled DNA. A stock solution of the purified labeled DNA was prepared by dissolving the dried product in a small volume of water. The DNA concentration and degree of labeling were determined as described in Example 3.

EXAMPLE 8

Preparation of Whole Chromosome #4 FITC-Labeled Paint Probe

DNA specific for the whole chromosome #4 was obtained, purified and sonicated as taught in Example 1 of Bittner et al., copending U.S. patent application Ser. No. 07/762,913, now U.S. Pat. No. 5,491,224, filed on even date herewith and identified by assignee's Docket No. 31,433, to provide DNA fragments with an average length of 300 bp. The fragmented DNA was aminated according to Example 1 of the present application by using the fragmented chromosome #4 DNA in place of the human total genomic DNA, and allowing the reaction to proceed for 15 hours at 25° C., to provide DNA with about 4 mole percent of the deoxycytidine nucleotides thereof transaminated. Following dialysis, phenol extraction and ethanol precipitation, 40 μg of the transaminated DNA was dissolved in 244 μl of 50 mM sodium borate at pH 9.3 and 6.1 μl of 50 mM FITC in dimethylsulfoxide added. The resulting solution was continually inverted overnight (approximately 18 hr) in the dark at room temperature. Following reaction, the DNA was precipitated with ethanol, in the same manner as described in Example 1. The dried product was dissolved in 300 μl of water and the solution applied to a 1 cm I.D.×30 cm high Econo-Column filled with Sephadex G-25 and eluted with water. The labeled material eluting at the column void volume was collected and again precipitated with ethanol to provide the purified labeled DNA. A stock solution of the purified labeled DNA was prepared by dissolving the dried product in a small volume of water. The DNA concentration and degree of labeling was determined as described in Example 3 (hereinabove).

EXAMPLE 9

Preparation of Whole Chromosome #4 Tx Rd-Labeled Paint Probe

DNA specific for the whole chromosome #4 (average fragment length of 300 bp) was prepared and aminated according to Example 8 above to provide DNA with 4.6 mole percent of the deoxycytidines transaminated. Following dialysis and ethanol precipitation, 40 μg of this DNA was dissolved in 270 μl of 50 mM sodium borate at pH 9.3 and 30 μl of 30 mM Tx Rd in dimethylformamide added. The resulting solution was continually inverted overnight (approximately 18 hr) in the dark at room temperature. Following reaction, the DNA was precipitated with ethanol, in the same manner as described in Example 1 above. The dried product was dissolved in 300 μl of water and the solution applied to a 1 cm I.D.×30 cm high Econo-Column filled with Sephadex G-25 and eluted with water. The labeled material eluting at the column void volume was collected and again precipitated with ethanol to provide the purified labeled DNA. A stock solution of the purified labeled DNA was prepared by dissolving the dried product in a small volume of water. The DNA concentration and degree of labeling were determined as described in Example 3.

EXAMPLE 10

Preparation of CTMR-Labeled Probe Composition Which is Specific to the Centromere of Human Chromosome #8

Transaminated DNA specific for the centromere of chromosome #8, designated #10-4 (average fragment length of 300 bp, 14 mole percent of the deoxycytidines transaminated), was obtained as described in the Bittner et al., copending application U.S. patent application Serial No. 07/762,912, now U.S. Pat. No. 5,506,350, filed on even date herewith and identified by assignee's Docket No. 30456. 40 μg of this DNA was dissolved in 362 μl of 0.2M 3-[N-morpholino]propanesulfonic acid at pH 7.4 and 38 μl of 30 mM CTMR in dimethylformamide added. The resulting solution was continually inverted overnight (approximately 18 hr) in the dark at room temperature. Following reaction, the product DNA was precipitated with ethanol, in the same manner as described in Example 1. The dried product was dissolved in 300 μl of water and the solution applied to a 1 cm I.D.×30 cm high Econo-Column filled with Sephadex G-25 and eluted with water. The labeled material eluting at the column void volume was collected and again precipitated with ethanol to provide the purified labeled DNA. A stock solution of the purified labeled DNA was prepared by dissolving the dried product in a small volume of water. The DNA concentration and degree of labeling were determined as described in Example 3.

EXAMPLE 11

Preparation of Whole Chromosome #8 CTMR-Labeled Paint Probe

DNA specific for the whole chromosome #8 (average fragment length of 300 bp) was prepared and transaminated according to Example 8 above to provide DNA with about 4 mole percent of the deoxycytidines transaminated. Following dialysis and ethanol precipitation, 750 μg of the DNA was dissolved in 6.66 ml of 0.2M 3-[N-morpholino] propanesulfonic acid at pH 7.4, 852 μl of 20 mM CTMR in dimethylformamide added, and the solution continually inverted overnight (approximately 18 hr) in the dark at room temperature. Following reaction, the DNA was precipitated with ethanol, in the same manner as described in Example 1. The dried product was dissolved in 2 ml of water and the solution applied to a 1.5 cm I.D.×48 cm high Econo-Column filled with Sephadex G-25 and eluted with water. The labeled material eluting at the column void volume was collected and again precipitated with ethanol to provide the purified labeled DNA. A stock solution of the purified labeled DNA was prepared by dissolving the dried product in a small volume of water. The DNA concentration and degree of labeling were determined as described in Example 3.

EXAMPLE 12

Preparation of Whole Chromosome #7 CTMR-Labeled Paint

DNA specific for the whole chromosome #7 (average fragment length of 300 bp) was prepared and aminated according to Example 8 above, except that the reaction time was increased to 48 hours to provide DNA with about 12 mole percent of the deoxycytidines transaminated. Following dialysis and ethanol precipitation, 1 mg of the DNA was dissolved in 8.88 ml of 0.2M 3-[N-morpholino] propanesulfonic acid at pH 7.4, 1.14 ml of 20 mM CTMR in dimethylformamide was added, and the solution was continually inverted overnight (about 18 hours) in the dark at room temperature. Following reaction, the DNA was precipitated with ethanol, in the same manner as described in Example 1. The dried product was dissolved in 2 ml of water and the solution applied to a 2.5 cm I.D.×48 cm high Econo-Column filled with Sephadex G-25 and eluted with water. The labeled material eluting at the column void volume was collected and again precipitated with ethanol to provide the purified labeled DNA. A stock solution of the purified labeled DNA was prepared by dissolving the dried product in a small volume of water. The DNA concentration and degree of labeling were determined as described in Example 3 above.

EXAMPLE 13

Preparation of Whole Chromosome #4 Biotin-Labeled Paint Probe

DNA specific for the whole chromosome #4 was obtained, purified, and sonicated as taught in Example 1 of Bittner et al., copending U.S. patent application Ser. No. 07/762,913, now U.S. Pat. No. 5,491,224, filed on even date herewith and identified by assignee's Docket No. 31,433, to provide DNA fragments with an average length of 300 bp. The DNA was transaminated according to Example 2 of the same copending application by using a reaction time of 48 hours and a reaction temperature of 37° C. to provide DNA with about 20% of the deoxycytidines transaminated. Following dialysis and ethanol precipitation, the aminated DNA was dissolved in 0.2M 3-[N-morpholino]propanesulfonic acid at pH 7.4 and a 100-fold molar excess of NHS-LC-Biotin (succinimidyl ester; Pierce cat. #21335) added. The excess was determined relative to the number of aminated deoxycytidines and the NHS-LC-Biotin was first dissolved at 0.2M in DMSO before adding to the DNA solution. The reaction was allowed to proceed overnight (approximately 18 hr) at room temperature. Following reaction, the DNA was precipitated with ethanol 3 times to provide the purified biotinylated probe.

EXAMPLE 14

Preparation of HCCA-Labeled Human Placental DNA

50 μg of transaminated DNA preparation #2 (12% dC transaminated) was dissolved in 444 μl of buffer consisting of 0.2M 3-[N-morpholino]propanesulfonic acid at pH 7.4, to this was added 57 μl of 20 mM HCCA in dimethylformanide and the solution was continually inverted overnight (about 18 hours) in the dark at room temperature. Following reaction, the DNA was precipitated with ethanol, in the same manner as described in Example 1. The dried product was dissolved in 300 μl of water and the solution applied to a 1 cm I.D.×30 cm high Econo-Column filled with Sephadex G-25 and eluted with water. The labeled material eluting at the column void volume was collected and again precipitated with ethanol to provide the purified labeled DNA. A stock solution of the purified labeled DNA was prepared by dissolving the dried product in a small volume of water. The DNA concentration and degree of labeling were determined as described in Example 3 above.

Table VI below summarizes the mole percent of fluorophores per total nucleotides in probe compositions hereinabove prepared:

TABLE VI

Percentage Labeling of Nucleotides with Fluorophores

| Proced. of Ex. No. | Fluorophore | Aminated DNA | % Fluorophore per nucleotide |
|---|---|---|---|
| Ex. 4.1 | CTMR | preparation #2 | 3.6 |
| Ex. 4.1 | CTMR | preparation #6 | 3.6 |
| Ex. 4.2 | CTMR | preparation #4 | 1.5 |
| Ex. 4.3 | CTMR | preparation #7 | 1.8 |
| Ex. 4.3 | CTMR | preparation #9 | 1.8 |
| Ex. 4.3 | CTMR | preparation #8 | 3.2 |
| Ex. 4.3 | CTMR | preparation #5 | 9.1 |
| Ex. 4.3 | CTMR | preparation #1 | 12 |
| Ex. 7 | AMCA | preparation #2 | 3.5 |
| Ex. 6 | DECCA | preparation #2 | 0.95 |
| Ex. 3 | FITC | preparation #4 | 0.29 (100 µg rx) |
|  |  |  | 0.30 (40 µg rx) |
| Ex. 3 | FITC | preparation #3 | 0.63 |
| Ex. 8 | FITC | whole chromosome #4 | 0.46 |
| Ex. 9 | Tx Rd | whole chromosome #4 | 1.0 |
| Ex. 11 | CTMR | whole chromosome #8 | 2.0 |
| Ex. 12 | CTMR | whole chromosome #7 | 3.0 |
| Ex. 5 | Tx Rd | preparation #4 | 0.76 |
| Ex. 10 | CTMR | chromosome #8 centromere | 3.0 |
| Ex. 14 | HCCA | preparation #2 | 1.1 |

EXAMPLE 15

In Situ Hybridizations

Each of the probe compositions of Examples 3 through 7 was evaluated for counterstaining capability in in situ hybridization. The target DNA consisted of cultured normal human white blood cells that were treated to arrest the cells in metaphase. These cells were dropped onto each of a plurality of glass microscope slides from about three feet to break open the nuclei.

The slides were then allowed to air dry and were stored at room temperature. Representative reagents and a procedure for performing the culturing and slide preparation are included in the TC Chromosome Culture Kit (DIFCO Laboratories, Detroit, Mich.).

(a) Genome Counterstaining

Each of the probe compositions of Examples 3 through 7 and Example 14 was evaluated for genome counterstaining capacity using the following procedure:

Using glass slides with specimen layers prepared as above described, just prior to hybridization each slide was denatured by placing the slide for 3 to 10 minutes in a 70° C. aqueous denaturing solution containing 70% formamide and 2×SCC at pH 7.0. The slide was then dehydrated by soaking the slide sequentially in 70%, 85%, and 100% ethanol baths, leaving the slide for 2 minutes in each bath, and the slide allowed to air dry.

The desired volume of labeled total genomic probe DNA stock solution (typically containing 25–600 µg of probe) was transferred with a pipette into a small plastic tube and the probe dried in a centrifugal evaporator (drying could be omitted if the volume was 3 µl or less). To the probe was added 7.0 µl of a solution containing 71.4% (v/v) formamide, 014.3% (w/v) dextran sulfate, 2.86×SSC at pH 7.0, unlabeled Cot-1 or human placental DNA in 3 µl or less of water if desired, and water to a final volume of 10 µl (final concentrations: 50% formamide, 10% dextran sulfate, 2×SSC). The tube containing the solution was then placed in a 70° C. water bath for 3–10 minutes for denaturation and then the 10 µl of hybridization solution applied directly to the denatured slide. This resulting slide was then covered with a coverslip, and the slide placed in a humidified chamber overnight at 37° C. To prevent evaporation or uptake of moisture, the edges of the coverslip were routinely sealed to the slide using rubber cement prior to placing the slide in the humidified chamber.

The next day, the coverslip was removed and the slide washed using either of two procedures. In Wash Procedure #1 the slide was soaked in a series of aqueous baths as follows: 15 minutes each in baths 1–3 containing 50% formamide and 2×SSC, pH 7, at 45° C., 15 minutes in bath 4 containing 2×SSC, pH7 at 45° C., 15 minutes in bath 5 containing 0.1M sodium phosphate, pH 7.0 and 0.1% (v/v) NP-40, at 45° C., and 2 minutes each in baths 6 and 7 containing 0.1M sodium phosphate, pH 7, and 0.1% NP-40 at room temperature. In Wash Procedure #2 the slide was soaked in a series of aqueous baths as follows: 10 minutes each in baths 1–3 containing 50% formamide and 2×SSC, pH 7, at 45° C., 10 minutes in bath 4 containing 2×SSC, pH 7, at 45° C., and 5 minutes in bath 5 containing 0.1M sodium phosphate, pH 7.0 and 0.1% (v/v) NP-40, at 45° C. After washing the slide was allowed to drain and air dried. 7.5 µl of antifade solution (see below) was applied directly to the slide and a coverslip was placed over the drop of antifade solution. Chemical counterstain could be applied to the specimen by including 0.2 µg propidium iodide/ml or 1.0 µg 4,6-diamidino-2-phenylindole hydrochloride (DAPI)/ml antifade solution. The slide could be viewed immediately or stored at −20° C. under nitrogen or argon (optionally slides could be stored at room temperature, in air, in the dark, for periods of several days). Antifade solution was prepared according to J. Immuno. Methods 43, 349 (1981) as follows: 100 milligrams of p-phenylenediamine dihydrochloride (Sigma Chemical Co., St. Louis, Mo.) was dissolved in 10 milliliters of phosphate buffered saline solution. The pH of this solution was adjusted to pH 8 with a bicarbonate buffer solution prepared by adding 0.42 g NaHCO₃ to 10 milliliters of water and adjusting the pH to 9.0 with the addition of 50% (w/v) NaOH. The pH adjusted solution of p-phenylenediamine dihydrochloride was added to 90 milliliters of glycerol and the resulting solution was filtered through a 0.22 µm filtration device. This solution is stored in the dark at −20° C.

Specimens stained by the total genomic DNA probes were also stained with one of the chemical counterstains DAPI or PI and the completeness of staining of the total genomic DNA probes and the chemical counterstains compared on the same metaphase spreads. Both the total genomic DNA probes and the chemical counterstains were found to stain the same material.

The results are summarized in Table VII below.

These results show that the probe compositions of Examples 3 through Example 14 result in complete counterstaining of all chromosomes present in the individual slide specimens evaluated.

(b) Genome Counterstaining Concurrently with a Chromosome Specific Paint Probe

Fluorophore-labeled human placental DNA and fluorophore-labeled chromosome-specific paint probes were simultaneously used in in situ hybridizations to provide staining of a specific pair of chromosomes in one fluorescent color and counterstaining of all chromosomes in a second color according to the following procedure:

Using glass slides with adhered specimen, the specimens were denatured and dehydrated just prior to hybridization as described above. The desired volume of labeled human placental DNA stock solution (typically containing 50–640 ng of probe) was transferred with a pipette into a small plastic tube along with the desired volume of labeled whole chromosome paint probe (typically containing 100–640 ng of probe), and the probe dried in a centrifugal evaporator. To the probe was added 7.0 μl of a solution containing 71.4% (v/v) formamide, 14.3% (w/v) dextran sulfate, and 2.86× SSC at pH 7.0, one microliter of blocking DNA, if used, comprised of unlabeled Cot-1 DNA (stock concentration=1 μg/1 μl), and water to a final volume of 10 μl (final concentrations: 50% formamide, 10% dextran sulfate, 2×SSC). The tube containing the solution was then placed in a 70° C. water bath for 3 to 10 minutes, and then 10 μl of the hybridization solution was applied directly to the denatured slide. The slide was then treated as in part (a) above to 1) hybridize overnight, 2) remove the unhybridized probe by washing, and 3) mount the slide for viewing under the fluorescence microscope.

Tables VII through×below show the details of the hybridization tests by in situ hybridization and provide a description of the human placental counterstain probe composition performance. For all the conditions shown, the chromosome targeted by the chromosome painting probe was stained specifically and distinctly with a fluorescent color different from that of the counterstain. These results show that the fluorescent human placental DNA probes provide a visually distinct and complete staining of all chromosomes and do not interfere with the hybridization of fluorescent chromosome painting probes when the two probe compositions are present simultaneously in an in situ hybridization.

TABLE VII

| Fluorophore-Labeled Genomic Probe Counterstaining | | |
|---|---|---|
| Probe Composition | ng probe in 10 μl hybridization solution | Results |
| HUMAN PLACENTAL DNA PROBES: | | |
| 1.5% CTMR-prep. #4 | 100 | very bright, even staining of all chromosomes. |
|  | 50 | bright, even staining of all chromosomes. |
| 3.6% CTMR-prep. #2 | 100 | very bright, even staining of all chromosomes. |
| 12% CTMR-prep. #1 | 100 | very bright, relatively uneven staining, many chromosomes contain localized bright spots (such as centromere regions), entire length and body of every chromosome stained to some extent. |
| 3.5% AMCA-prep. #2 | 300 | weak, even staining of all chromosomes. |
|  | 600 | moderately intense even staining of all chromosomes. |
| 1.1% HCCA-prep. #2 | 300 | bright, even staining of all chromosomes. |
|  | 600 | bright, even staining of all chromosomes. |
| 0.95% DECCA-prep. #2 | 640 | bright, even staining of all chromosomes. |
| 0.29% FITC-prep.#4 | 320 | bright, even staining of all chromosomes. |
| 0.76% Tx Rd-prep. #4 | 100 | bright, even staining of all chromosomes. |
| $C_o$t-1 DNA PROBES: | | |
| 1.8% CTMR-prep. #7 | 100 | bright, relatively uneven staining, many chromosomes contain localized bright spots (such as centromere regions), entire length and body of every chromosome stained to some extent. |
| 3.6% CTMR-prep. #5 | 100 | very bright, uneven staining, many chromosomes contain localized bright spots (such as centromere regions), entire length and body of every chromosome stained to some extent. |
| 9.1% CTMR-prep. #5 | 100 | bright, uneven staining, many chromosomes contain localized bright spots (such as centromere regions), entire length and body of every chromosome stained to some extent. |
| COSMID LIBRARY PROBES: | | |
| 1.8% CTMR-prep. #9 | 100 | bright, uneven staining, chromosomes contain brighter and darker regions, the variations in stain intensity are more complex than observed with the $C_o$T-1 DNA probes, entire length and body of every chrmosome stained to some extent. |
| 3.2% CTMR-prep. #8 | 100 | bright, uneven staining, chromosomes contain brighter and darker regions, the variations in stain intensity are more complex than observed with the $C_o$t-1 DNA probes, entire length and body of every chromosome stained to some extent. |

TABLE VIII

CTMR-Human Placental DNA Counterstain Used with FITC-Labeled Whole Chromosome #4 Paint Probe. (No additional blocking DNA was used.)

| (1) [CTMR-H.P.] (ng/10 µl) | (2) [FITC-C4] (ng/10 µl) | (3) Visual Description of Counterstain (slide under microscope-40×) | |
|---|---|---|---|
| | | (4) Completeness | (5) Intensity |
| 32 | 316 | +++ | ++ |
| 100 | 316 | +++ | ++++ |
| 320 | 316 | +++ | ++++ |
| 1000 | 316 | ++ | ++++ |
| 3200 | 316 | ++ | ++++ |

Table VIII Footnotes:
(1) H.P. designates human placental DNA segments.
(2) C4 designates human chromosome #4 DNA segments.
(3) Code for Visual Description shown in following footnotes (4) and (5).
(4) Completeness - (−) nonuniform counterstaining, (+) uniform counterstaining but very uneven coverage of chromsomes with counterstain, (++) uniform coverage of chromosomes with some regions of the chromosomes stained considerably brighter than other regions, (+++) uniform and even coverage of chromosomes with counterstain.
(5) Intensity - (−) not visible, (+) barely visible, (++) fairly visible, (+++) bright, (++++) very bright

TABLE IX

FITC-Human Placental DNA Counterstain Used with Texas Red-Labeled Whole Chromosome #4 Paint Probe (No additional blocking DNA was used.)

| (4) [FITC-H.P.] (ng/10 µl) | (5) [TxRd-C4] (ng/10 µl) | (1) Visual Description of Counterstain (slide under microscope-40×) | |
|---|---|---|---|
| | | (2) Completeness | (3) Intensity |
| 100 | 200 | +++ | +++ |
| 320 | 200 | +++ | ++++ |

Table IX Footnotes:
(1) Code for Visual Description shown in following footnotes (2) and (3).
(2) Completeness - (−) nonuniform counterstaining, (+) uniform counterstaining but very uneven coverage of chromosomes with counterstain, (++) uniform coverage of chromosomes with some regions of the chromosomes stained considerably brighter than other regions, (+++) uniform and even coverage of chromsomes with counterstain.
(3) Intensity - (−) not visible, (+) barely visible, (++) fairly visible, (+++) bright, (++++) very bright
(4) H.P. designates human placental DNA segments.
(5) C4 designates human chromosome #4 DNA segments.

TABLE X

DECCA-Human Placental DNA Counterstain Used with CTMR-Labeled Whole Chromosome #8 Paint Probe. (1 µg of $C_0t$-1 Blocking DNA was used in each 10 µl of counterstain)

| (4) [DECCA-H.P.] (ng/10 µl) | (5) [CTMR-C8] (ng/10 µl) | (1) Visual Description of Counterstain (slide under microscope-40×) | |
|---|---|---|---|
| | | (2) Completeness | (3) Intensity |
| 600 | 100 | +++ | +++ |

Table X Footnotes:
(1) Code for Visual Description shown in following footnotes (2) and (3).

TABLE X-continued

DECCA-Human Placental DNA Counterstain Used with CTMR-Labeled Whole Chromosome #8 Paint Probe. (1 µg of $C_0t$-1 Blocking DNA was used in each 10 µl of counterstain)

| (4) [DECCA-H.P.] (ng/10 µl) | (5) [CTMR-C8] (ng/10 µl) | (1) Visual Description of Counterstain (slide under microscope-40×) | |
|---|---|---|---|
| | | (2) Completeness | (3) Intensity |

(2) Completeness - (−) nonuniform counterstaining, (+) uniform counterstaining but very uneven coverage of chromosomes with counterstain, (++) uniform coverage of chromsomes with some regions of the chromsomes stained considerably brighter than other regions, (+++) uniform and even coverage of chromosomes with counterstain.
(3) Intensity - (−) not visible, (+) barely visible, (++) fairly visible, (+++) bright, (++++) very bright
(4) H.P. designates human placemental DNA segments.
(5) C4 designates human chromosomes #8 DNA segments.

(c) Genome Counterstaining Concurrently with a Chromosome Centromere Specific Probe Fluorophore-labeled human placental DNA and fluorophore-labeled centromere-specific probes were simultaneously used in in situ hybridizations to provide staining of a specific pair of chromosome centromeres in one fluorescent color and counterstaining of all chromosomes in a second color according to the following procedure:

Using glass slides with adhered specimens, the specimens were denatured and dehydrated just prior to hybridization as described above. The desired volume of 0.30% FITC-preparation #4 stock solution was transferred with a pipette into a small plastic tube along with the desired volume of 3% CTMR-chromosome #8 centromere specific probe stock solution, and the probe dried in a centrifugal evaporator. To the probe was added 7.0 µl of a solution containing 78.6% (v/v) formamide, 14.3% (w/v) dextran sulfate, 2.86×SSC at pH 7.0, 2–4 µg of unlabeled sonicated human placental DNA to serve as blocking DNA, and water to a final volume of 10 µl (final concentrations: 55% formamide, 10% dextran sulfate, 2×SSC). The tube containing the solution was then placed in a 70° C. water bath for about 3 to 10 minutes, and then the 10 µl of hybridization solution was applied directly to the denatured slide. This slide was then treated as in part (a) above to 1) hybridize overnight, 2) remove the hybridized probe by washing (Wash Procedure 1), and 3) mount the slide for viewing under the fluorescence microscope, with the one exception that the overnight hybridization was conducted at 42° C. instead of 37° C.

Table XI below shows the details of the hybridization tests by in situ hybridization together with a description of the human placental counterstain performance. For all the conditions shown, the chromosome #8 centromere was stained specifically and distinctly with an orange fluorescence distinct from that of the green fluorescent counterstain. These results show that the fluorescent human placental DNA probes provide a visually distinct and complete staining of all chromosomes and do not interfere with the hybridization of fluorescent chromosome centromere-specific probes when the two probe compositions are present simultaneously in an in situ hybridization.

TABLE XI

FITC-Human Placental Counterstain Used with CTMR-Labeled Chromosomes #8 Centromere-Specific Probe

| | | (1) Visual Description of Counterstain (slide under microscope-40×) | |
|---|---|---|---|
| (4) | (5) | (2) | (3) |
| \|FITC-H.P.\| (ng/10 µl) | \|CTMR-Cen#8\| (ng/10 µl) | Completeness | Intensity |
| 100 | 32 | +++ | ++++ |
| 320 | 32 | +++ | ++++ |

Table XI Footnotes:
(1) Code for Visual Description shown in following footnotes (2) and (3).
(2) Completeness - (−) nonuniform counterstaining, (+) uniform counterstaining but very uneven coverage of chromosomes with counterstain, (++) uniform coverage of chromosomes with some regions of the chromosomes stained considerably brighter than otehr regions, (+++) uniform and even coverage of chromsomes with counterstain.
(3) Intensity - (−) not visible, (+) barely visible, (++) fairly visible, (+++) bright, (++++) very bright
(4) H.P. designates human placental DNA segments.
(5) Cen #8 designates DNA segments complementary to human chromosome #8 centromere only.

(d) Sequential Staining: In Situ Hybridization with Labeled Human Placental DNA Followed by In Situ Hybridization with Labeled Chromosome Painting Probe FITC-labeled human placental DNA and CTMR-labeled chromosome painting probes were sequentially used in in situ hybridizations to provide staining of a specific pair of chromosomes in one fluorescent color and counterstaining of all chromosomes in a second color according to the following procedure:

Using glass slides with adhered specimens of the human genome, the specimens were denatured and dehydrated just prior to hybridization as described above. 2.23 µl of 0.29% FITC-preparation #4 stock solution (600 ng probe) was transferred with a pipette into a small plastic tube and the probe composition dried in a centrifugal evaporator. To the probe was added 7.0 µl of a solution containing 71.4% (v/v) formamide, 14.3% (w/v) dextran sulfate, and 2.86×SSC at pH 7.0, and water to a final volume of 10 µl (final concentrations: 50% formamide, 10% dextran sulfate, and 2×SSC). The tube containing the solution was then placed in a 70° water bath for 5 minutes, and the 10 µl of hybridization solution was applied directly to the denatured slide. The slide was then treated as in part (a) above to 1) hybridize overnight, 2) remove the unhybridized probe by washing (Wash Procedure 2), and 3) mount the slide for viewing under the fluorescence microscope.

After viewing the stained specimen, the specimen was prepared for the second hybridization by removing the coverslip and washing the slide for 30 minutes in an aqueous bath containing 2×SSC and 0.1% NP40, pH7.0, at room temperature, to remove the mounting medium. The slide was then drained and air dried. 3.33 µl of 2.0% CTMR-whole chromosome #8 painting probe composition stock solution prepared as hereinabove described (100 ng) was transferred with a pipette into a small plastic tube and the probe composition dried in a centrifugal evaporator. To the probe composition was added 7.0 µl of a solution containing 71.4 (v/v) formamide, 14.3% (w/v) dextran sulfate, 2.86×SSC at pH 7.0, 1 µl of Cot-1 DNA (1 µg of Cot-1 DNA/µl stock solution) for blocking DNA, and water to a final volume of 10 µl(final concentrations: 50% formamide, 10% dextran sulfate, 2×SSC). The tube containing the solution was then placed in a 70° C. water bath for 5 minutes, and the 10 µl of hybridization solution was applied directly to the slide. The slide was then treated as in part (a) above to 1) hybridize overnight, 2) remove the unhybridized probe by washing (Wash Procedure 2), and 3) mount the slide for viewing under the fluorescence microscope.

After the first hybridization, examination under the fluorescence microscope showed uniform FITC staining (green fluorescence) of all chromosomes with good intensity. After the second hybridization, the intensity of the FITC staining was somewhat reduced, but was still uniform and easily discerned. In addition, bright and specific CTMR staining (orange fluorescence) of a single pair of chromosomes was observed. Thus, the counterstain probe composition completely stains genomic DNA in such a successive staining procedure using two different probe compositions with the same specimen.

(e) Sequential DNA Staining: In Situ Hybridization with Labeled Chromosome Painting Probe Composition Followed by In Situ Hybridization with Labeled Human Placental DNA CTMR-labeled chromosome painting probes and DECCA-labeled human placental DNA were sequentially used in hybridizations to provide staining of a specific pair of chromosomes in one fluorescent color and counterstaining of all chromosomes in a second color according to the following procedure:

Using glass slides with adhered specimens, the specimens were denatured and dehydrated just prior to hybridization as above described. 3.33 µl of 3.0% CTMR-whole chromosome #7 painting probe composition stock solution prepared as above described (100 ng probe) was transferred with a pipette into a small plastic tube and the probe composition dried in a centrifugal evaporator. To the dried probe composition was added 7.0 µl of a solution containing 71.4% (v/v) formamide, 14.3% (w/v) dextran sulfate, and 2.86× SSC at pH 7.0, 1 µl of Cot-1 DNA (1 µg of Cot-1 DNA/1 µl stock solution) for blocking DNA, and water to a final volume of 10 µl (final concentrations: 50% formamide, 10% dextran sulfate, 2×SSC). This 10 µl of hybridization solution was applied directly to the denatured slide and the slide treated as in part (a) above to 1) hybridize overnight, 2) remove unhybridized probe by washing (Wash Procedure 2), and 3) mount the slide for viewing under the fluorescence microscope.

After viewing the stained specimen, the specimen was prepared for the second hybridization by removing the coverslip and washing the slide for 30 minutes in a bath containing 2×SSC and 0.1% NP40, pH 7.0, at room temperature, to remove the mounting medium. The slide was then drained and air dried. 2.68 µl of 0.95% DECCA-preparation #2 stock solution (300 ng probe) was transferred with a pipette into a small plastic tube and the probe dried in a centrifugal evaporator. To the probe was added 7.0 µl of a solution containing 71.4% (v/v) formamide, 14.3 % (w/v) dextran sulfate, and 2.86×SSC at pH 7.0, and water to a final volume of 10 µl (final concentrations: 50% formamide, 10% dextran sulfate, and 2×SSC). The tube containing the solution was then placed in a 70° C. water bath for 5 minutes, and the 10 µl of hybridization solution was applied directly to the slide. The slide was then treated as in part (a) to 1) hybridize overnight, 2) remove the unhybridized probe by washing (Wash Procedure 2), and 3 mount the slide for viewing under the fluorescence microscope.

After the first hybridization, examination under the fluorescence microscope showed bright and specific CTMR staining (orange fluorescence) of a single pair of chromosomes. After the second hybridization, the intensity of the CTMR staining was somewhat reduced, but it was still fairly bright and was easily discerned. In addition, complete DECCA staining (aqua fluorescence) of all chromosomes, with good intensity, was observed.

(f) Genome Counterstaining Concurrently with a Biotin Labeled Chromosome Paint Probe (Direct Fluorophore Labeled Genomic Probe and Indirect Labeled Chromosome Paint Probe The hybridization was performed essentially the same as in Example 15 (a) except that 100 ng of biotin labeled probe of Example 13 was included with 100 ng of 1.5% CMTR labeled preparation #4 and 1 µg of Cot-1 DNA in the 10 µl hybridization solution. In addition several post-hybridization incubations were required to bind the indirect labeling reagents as follows. After the overnight hybridization the slide was washed (wash procedure #1) and then incubated in a solution of 5 µg fluorescein streptavidin (obtained from Vector Labs, Burlingame, Calif.) per ml of PMN buffer (PMN buffer=0.1M sodium phosphate at pH=7.0, 0.1% (w/v) NP-40, 0.2% sodium azide, and 5% nonfat dry milk) for 20 minutes at room temperature. The slide was then washed twice in PN buffer (PN buffer=0.1M sodium phosphate and 0.1% (w/v) NP-40 at pH 7.0) for 2 minutes each time at room temperature and then incubated in a solution of 5 µg biotinylated anti-streptavidin (obtained from Vector Labs) per ml of PMN buffer for 20 minutes at room temperature. The slide was then washed twice in PN buffer, 2 minutes each time, at room temperature, and incubated in a solution of fluorescein streptavidin (same as above) for 20 minutes at room temperature. The slide was then washed a final two times in PN buffer, 2 minutes each time, and the slide allowed to drain and air dry before applying the antifade solution, covering with a coverslip, and viewing under the fluorescence microscope.

Examination under the fluorescence microscope showed bright and specific green staining of a single pair of metaphase chromosomes together with bright and complete orange staining of all of the chromosomes. This result shows that the direct label human placental DNA probe provides a visually distinct genomic counterstaining which is not adversely affected by the post-hybridization labeling reactions required by the indirect label probe and which does not interfere with the hybridization and post-hybridization reactions of the indirect label probe.

Other and further embodiments will be apparent to those skilled in the art from the preceding description and Examples. No unreasonable limitations or the like are to be drawn therefrom.

What is claimed is:

1. A process for identifying genomic DNA present in a specimen that is derived from a multichromosomal organism comprising the steps of sequentially:
   (a) contacting said specimen under hybridizing conditions with a direct label probe composition for counterstaining genomic DNA present in the specimen, wherein the direct label probe composition comprises a mixture of deoxyribonucleic acid segments which are covalently bound to fluorophore groups through linking groups, said deoxyribonucleic acid segments (i) having been derived from the total genomic DNA of the multichromosomal organism from which the genomic DNA present in the specimen was derived and (ii) being approximately representative of said total genomic DNA, so as to produce hybrids between said genomic DNA and probe deoxyribonucleic acid segments present in said probe composition;
   (b) separating from the resulting said specimen residual portions of said probe composition; and
   (c) examining said resulting specimen by irradiating same with energy which is at least sufficient to cause fluorophore groups present in said hybrids to fluoresce while concurrently detecting the resulting fluorescent energy so produced, thereby identifying said genomic DNA present in said specimen.

2. The process of claim 1 wherein:
   (a) said specimen is comprised of cytological material that is distributed as a solid adhering layer upon one surface of a slide;
   (b) said contacting is carried out by applying an aqueous solution of said probe composition to said specimen using hybridizing conditions;
   (c) said separating is carried out by washing said resulting specimen with an aqueous liquid; and
   (d) said examining is carried out with a fluorescence microscope.

3. The process of claim 1 wherein:
   (a) said specimen is comprised of an aqueous suspension of chromosomes;
   (b) said contacting is carried out by dissolving said probe composition in said suspension;
   (c) said separating is carried out by centrifuging; and
   (d) said examining is carried out with a flow cytometer.

4. The process of claim 3 wherein after said contacting, the concentration of residual said probe composition is so low as not to interfere with said examining, and said separating step is not performed.

5. The process of claim 1 wherein, prior to said contacting, said probe composition is admixed with at least one additional different probe composition and each of said additional probe compositions is targeted to a predetermined fractional region of said genomic DNA.

6. The process of claim 5 wherein each of said additional probe compositions incorporates directly detectable fluorophore groups whose respective associated observable color under fluorescing microscopic conditions is different from the observable color of the fluorophore groups in said probe composition under such conditions.

7. The process of claim 5 wherein one additional probe composition is so admixed and said one additional probe composition hybridizes with a single predetermined particular chromosome of said genomic DNA, if such chromosome is present in said specimen, during said contacting.

8. The process of claim 5 wherein one additional probe composition is so admixed and said one additional probe composition hybridizes to a centromere region of a single predetermined particular chromosome of said genomic DNA, if said centromere region is present in said specimen, during said contacting.

9. The process of claim 5 wherein at least one of said additional different probe compositions is an indirect label probe composition.

10. The method of claim 5 wherein said deoxyribonucleic acid segments are derived from a fragmented library of human total genomic DNA.

11. The method of claim 6 wherein said deoxyribonucleic acid segments are derived from a fragmented library of human total genomic DNA.

12. The process of claim 1 wherein, prior to step (c), the sequence of said steps (a) and (b) is repeated at least once, and in each said repeat, a different probe composition is employed with the direct label probe composition for counterstaining genomic DNA present in a specimen being used once, and with each of such other probe compositions being targeted to a different predetermined fractional region of said genomic DNA.

13. The process of claim 1 wherein said genomic DNA is the human genome.

14. The method of claim 1 wherein said deoxyribonucleic acid segments are derived from a fragmented library of human total genomic DNA.

15. The method of claim 1 wherein said deoxyribonucleic acid segments comprise Cot-1 DNA.

16. The method of claim 1 wherein said fluorophore groups comprise 5-(and-6)-carboxytetramethylrhodamine, succinimidyl ester.

* * * * *